(12) United States Patent
Vuong

(10) Patent No.: US 9,398,058 B2
(45) Date of Patent: Jul. 19, 2016

(54) SYSTEMS AND METHODS FOR VIDEO-CONFERENCE NETWORK SYSTEM SUITABLE FOR SCALABLE, PRIVATE TELE-CONSULTATION

(71) Applicant: Tony Thang Vuong, Milpitas, CA (US)

(72) Inventor: Tony Thang Vuong, Milpitas, CA (US)

(73) Assignee: InstaMedica Inc., San Jose, CA (US)

( * ) Notice: Subject to any disclaimer, the term of this patent is extended or adjusted under 35 U.S.C. 154(b) by 226 days.

(21) Appl. No.: 14/065,395

(22) Filed: Oct. 28, 2013

(65) Prior Publication Data

US 2015/0120827 A1 Apr. 30, 2015

(51) Int. Cl.
*G06F 15/16* (2006.01)
*H04L 29/06* (2006.01)
*H04L 29/08* (2006.01)
*G06Q 50/00* (2012.01)

(52) U.S. Cl.
CPC .............. *H04L 65/403* (2013.01); *G06Q 50/01* (2013.01); *H04L 67/12* (2013.01); *H04L 67/24* (2013.01)

(58) Field of Classification Search
CPC .................................................... H04L 65/403
See application file for complete search history.

(56) References Cited

U.S. PATENT DOCUMENTS

| 7,684,397 B2 * | 3/2010 | Kim | H04L 29/12009 370/389 |
| 7,962,627 B2 * | 6/2011 | Lin | H04L 29/12509 709/227 |
| 2010/0077087 A1 * | 3/2010 | Roy | H04L 29/1249 709/228 |
| 2010/0146048 A1 * | 6/2010 | Rothstein | G06F 17/3089 709/204 |

OTHER PUBLICATIONS

Poulin et al, NAT Traversal in Peer-To-Peer Architecture, Tech Report SCE-12-04, 2004.

* cited by examiner

*Primary Examiner* — Vivek Srivastava
*Assistant Examiner* — Nicholas Celani
(74) *Attorney, Agent, or Firm* — Tran & Associates

(57) ABSTRACT

A scalable social network consultation communication system for teleconsultation private practice includes a social network, a social network processing system, video conferencing equipment coupled to the social network to allow a consultation requestor to communicate with a predetermined advisor, a store and forward infrastructure to receive a consultation request from a consultation requestor, wherein the consultation requestor selects and passes a consultation request to a predetermined advisor on the social network, and wherein the advisor resolves and returns the consultation resolution of the consultation request to the consultation requestor.

9 Claims, 15 Drawing Sheets

SYSTEMS AND METHODS FOR VIDEO-CONFERENCE NETWORK SYSTEM SUITABLE FOR SCALABLE, PRIVATE TELE-CONSULTATION

BACKGROUND

The present invention relates to systems and methods for telemedicine.

Telemedicine is the practice of collaborative medicine over a telecommunication network of sites grouped into hubs and spokes, between consultation providers at hub sites that provide the consultation service, and consulters at spoke sites that request and use the service. In a small setting of telemedicine practice, a plurality of physicians form and work together in a health alliance group to serve either a plurality of clients who are lesser experienced physicians who then serve the local patients, or to serve directly to a plurality of clients who are patients themselves, for extended hours of days of a week, for example, a tele-consultation service that is "24/7" will mean non-stop, "24 hours by 7 days of a week".

The consultations between two parties that are remote from each other are not well supported using existing solutions. In such consultations, a $1^{st}$ party as "consulter" looking for solution, and a $2^{nd}$ party as "consultant", also referred as "advisor" providing such solution, communicate using audio/video devices and the connected Internet network media (tele-consultation). Existing network telemedicine solutions are based on sophisticated video conference equipment for large network installation, enhanced with workflow medical case management developed around central hubs. The solutions are difficult to set up, expensive to maintain, exposed to bottle-neck weakness at high traffic, and contain a many hidden costs.

For example, at existing central hubs, the effort to setup and maintain a central web portal equipped for high-speed, high quality, multi-media store-forward traffic is lengthy, costly, and requires knowledgeable personnel. Also at the central hub, the network arrangement to service multiple interactive video conference calls typically requires installing specialized network conference equipment that small private practices cannot afford. At satellite spoke sites, the telemedicine devices and equipment marketed by the existing network telemedicine solutions are also designed to work with and for a central hub. They are built to capture and submit unfiltered data to the central hub's database, thus contribute to high-traffic load at the central web portal, and add cost to manage unessential data. Furthermore, these new devices and equipment are not designed to be integrated easily into existing solutions: they typically are prepackaged for a few specialty categories, hence are not adaptable for additional categories beyond their instrumentation. Thus, they are not compatible with existing equipment that are essential to the current practice of many hospitals and clinics around the world.

As discussed in Pulin et al.'s technical report entitled "NAT Traversal in Per-to-Peer Architecture", peer-to-peer networks are well known for file sharing between multiple computers. They establish virtual tunnels between computers to transfer data, but NATs makes it harder. A NAT, Network Address Translation, is a process which transforms private IP addresses, such as 192.168.2.1, into public addresses, such as 203.0.113.40. The idea is that multiple private addresses can hide behind a single public address and thus virtually enlarge the number of allocable public IP addresses. When an application in the local network establishes a connection to Internet, the packet passes through the NAT which adjusts the IP header and maps an external port to the computer which sent the request. When packets are received from the Internet by the NAT, they are forwarded to the internal host which is mapped to the port on which the packet was received, or dropped if no mapping exists.

High-bandwidth multi-media communication network systems to provide communication service to users and devices behind NAT (network address translator) routers are gaining popularity as users look beyond just simply peer-peer voice communication. U.S. Pat. No. 7,962,627 B2 and U.S. Pat. No. 7,684,397 B2 disclose media and systems for peer-to-peer network address translator (NAT) traversal techniques where the functions of STUN (Simple Traversal of UDP over NAT) and TURN (Traversal Using Relay NAT) servers are described and disclosed. United States Patent 20100077087 discloses a method and system for a network peer system to collect NAT profile information from other peers and share said NAT profile information to other peers.

In a parallel trend, social network systems coupled with multi-media communication network systems are also known. United States Patent Application 20100146048 discloses social network systems and methods. The system includes at least one computer which provides content to a first group of members and a second group of members. A first portion of the content is associated with a first social network and a second portion of the content is associated with a second social network. The first social network is associated with a first entity, and the first group of members. The first portion of the content includes first member-generated content. The second social network is associated with a second entity and the second group of members. The second portion of the content includes second member-generated content. The computer provides to the first group of members: (i) the first member-generated content, and (ii) at least a portion of the second member-generated content.

SUMMARY OF THE INVENTION

In one aspect, systems and methods are analyzed for a multi-party conferencing network system to connect peers in a constellation topology from a lesser number of hubs to a greater number of spokes wherein the connectivity can be optimized in a majority of connecting cases by initiating connection sessions from the spoke side which normally runs in private addressing mode to the hub side which is normally runs in public addressing mode. The addressing mode identification of peers in a session is crucial to the method to provide conference bridging of the peers together.

In another aspect, systems and methods are described for a store and forward infrastructure between peer servers also in a constellation topology wherein a submitting spoke server stores a consultation unit connects to a resolution hub server in order to forward a consultation request from a consultation requestor to a consultation advisor.

In yet another aspect, a social network consultation communication system includes a store and forward infrastructure to receive a consultation request from a consultation requestor, a social network coupled to the store-and-forward infrastructure to select and pass the consultation request to a predetermined advisor on the social network, and video conferencing equipment coupled to the social network and the store-and-forward infrastructure to allow the consultation requestor to communicate with the predetermined advisor.

Advantages of the social network consultation communication system in the field of teleconsultation in telemedicine may include one or more of the following. The system allows members of a small physician group or alliance who needs a solution to practice tele-consultation to the clients or the patients in a private, easy to operate setting. The system allows features such as data security and connection privacy, high-grade direct video conferencing and store-forward consult management workflow. The system also allows unhindered connectivity between mobile-able physicians and patients in a 24/7 setting, as well as adaptability of new equipment and new practice to augment the existent current practice. As the alliance expands to a large telemedicine network, the solution can scale easily and avoid high load concentration at a central hub that can be catastrophic. The system achieves scalability through a scalable, peer-peer network system architecture with distributable servers, increases business volume with an upgradable strategy to integrate new equipment and practices, and allow new markets and international expansion through mediation gateways. As such, the system provides tele-consultation service administrators the tools they need to gradually and effectively integrate new tele-consultation services alongside with already available services.

Although the foregoing discusses systems for teleconsultation in telemedicine, such tele-health consultation is merely one embodiment of an applicable field of the invention. There are many other fields in teleconsultation that are also applicable embodiments of the invention, namely manufacturing, automotive, construction, food processing, apparels, education, among others.

BRIEF DESCRIPTION OF THE DRAWINGS

Embodiments of the invention will now be described with reference to the accompanying drawings wherein.

Figure 1A:
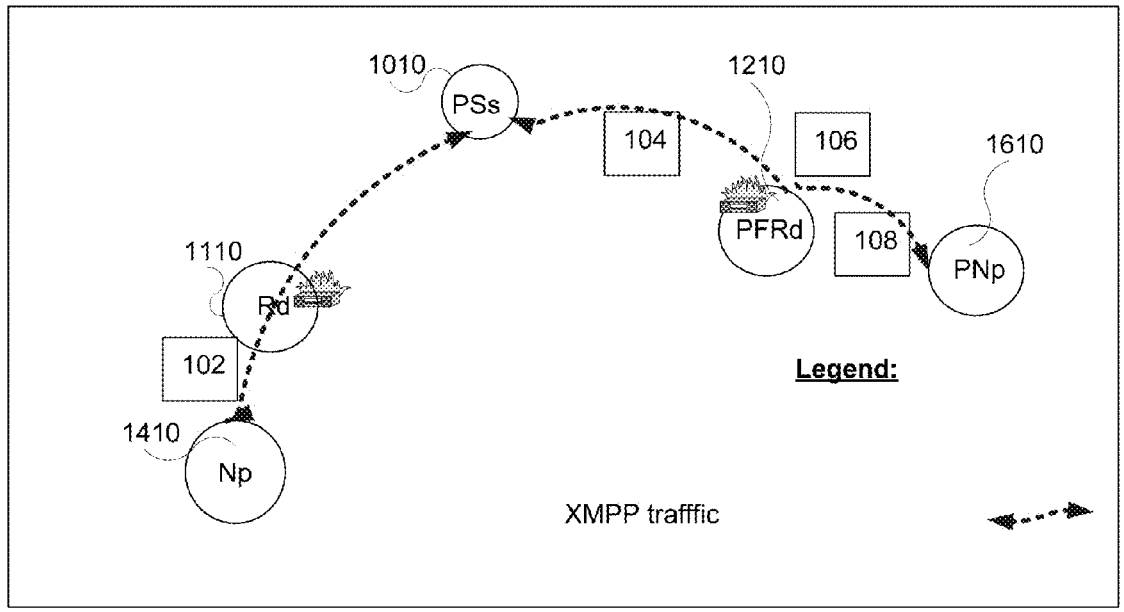
FIG. 1A shows exemplary network entities in a social network system for audio/video/text/file chat.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DESCRIPTION

The following is to capture an embodiment of one of the many applicable services of the invention, which is particularly in this embodiment associated to tele-consultation in the field of medical and health-care, also known as telemedicine. It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

First Embodiment

Network Entities in a Social Network System for Private Consultation Practice

FIG. 1A shows a preferred embodiment of network entities to support interactive audio/video/text/file chatting between peers. In a social network system, users can reach other users by logging in and communicating to a Public Social server (PSs) 1010 using a social networking client program that supports a protocol such as the Extensible Messaging and Presence Protocol (XMPP) to announce their presence for interactive services such as chatting or gaming. To allow for mobility servers that move with users, a peer-to-peer (P2P) social network system also supports end clients of the social network services that are also servers. End-to-end servers that are distributed in a social network system, and that also support standard security protocols and services, are highly secured, since all network data are not concentrated a single central server place where all metadata of the network data is available.

In a private practice tele-consultation social network system, the users are typically grouped into hubs and spokes, the consult providers at hub sites that provide the consultation service, and consulters at spoke sites that request and use the service. Furthermore, for users in an application embodiment of the invention, specifically in telemedicine social network system, the practice of medicine requires the highest available audio/video performance that the network is able to provide. In a preferred embodiment that is the basis for providing optimal network performance and security for large mobile clients at spokes and also for a smaller number of mobile clients at hubs, the system focuses on supporting network entities with specific configuration as embodied in FIG. 1A as follows:

Public-Social-server (PSs) 1010: A single hosting central system or a centralized network of systems that comprises two sub-level central server subsystems, a 1st central server subsystem for a social network communication system and a 2nd central server subsystem for a multi-media multi-party conference system. Theoretically said 2 central subsystems can be logically separated; however, in practice, since a social network communication is tightly coupled to a multi-media multi-party conference system, the two central subsystems are typically combined in one. A PSs comprises at least a component social network server. This server keeps records of all active, logged-in peers' IP host address attributes and NAT-related address attributes reported by its communication servers as well as reported by each peer. A PSs is responsible for the management of all said records is its social network addressing domain. Examples of component social network servers of said 1st central subsystem are XMPP-based social server or SIP-based social server. Examples of component servers of said 2nd central server subsystem are STUN and TURN servers required for NAT-related discovery as referenced in U.S. Pat. No. 7,684,397 B2. For all peers in a social network addressing domain, PSs is a well-known server. It should be advisable to reader that the component servers of a PSs do not have to be collocated in a single system host—instead, they can be hosted in multiple networked systems that function together to provide the combined functionality of said PSs.

NATed-peer (Np) 1410: A client of the social network system using the social network protocol of the system to communicate to other peers wherein the host system of the client in a private network is allowed only "private addressing mode" operation as it is located behind a plurality of NAT layers wherein the combination of NAT firewalls and NAT routers forces the system to establish only sessions from internet outbound calls. A mobile consulter at a spoke site seeking consulting service typically uses an Np system and methods to communicate to other peers.

Router-device (Rd) 1110: A commercial-off-the-shelf (COTS) consumer router device that performs routing function to connect local devices to the Internet. Typically the router device supports two vital functions for local devices: (a) network-address translation (NAT) and (b) firewall security protection.

Privilege-Forwarding-Router-device (PFRd) 1210: A router device on the system that has a plurality of public IP addresses, wherein the router is configured to support one or more port—forwarding privilege profiles for a user, wherein each privilege profile defines authentications, protocols, and ranges of public IP addressable ports that said privilege user can use to log in to the router, to configure said router to perform port-forwarding said range of public IP addressable ports to the host system the user currently runs in. An exemplary case of a common port-forwarding privilege profile is coupled with UPnP being enabled for a router then a universal privilege profile is associated and is enabled for each internal router user who runs on the local segment attached to said router using UPnP protocol. On the other hand, if only UPnP is enabled for a user who has an Secured Shell (SSH) account or a Virtual Private Network (VPN) account to a router and who can executes appropriate UPnP instructions after SSH-logging or VPN-logging, then the port-forwarding privilege is only enabled for said user.

It is apparent to those skilled in the art that the above requirement for a PFRd or a network entity to have a plurality of public IP addresses is appropriate if the IP address domain of said PFRd or said network entity is WAN or Internet-wide. If however, the IP address domain of said PFRd or said network entity is a private LAN or a Virtual Private Network (VPN), then the requirement of a plurality of public IP addresses is reduced to only a plurality of IP addresses well-known to all network peers in said IP address domain.

Privileged-NATed-peer (PNp) 1610: A specific client of the social network system that typically runs at a hub site to connect to other peers at spoke sites, wherein the host system of the client, although is located in a private network behind multiple NAT layers, is allowed also "public addressing mode" operation on a public IP router that said host system connects to wherein said host system is allowed to establish communication endpoints on this router that channel traffic to said host system itself, and is also allowed to configure port-forwarding operation on a plurality of public IP addressable ports on the public router to forward internet inbound calls to the port-forwarding ports to said host system. To function properly PNp needs to engage a relay operation at the router. PNp requires a special privilege at the PFRd router, allowing its current user to login at PFRd and reconfigure a small subset of ports to be used as data channels for communication to other peers. The subset of public IP addressable ports for a PNp agent system to use on behalf of its user for purpose of appearing publicly to the Internet during said user's login time can by dynamic and can be restricted to avoid security and performance impact to traffic on the router.

In FIG. 1A, all clients must login to PSs to use the services of the social network system. Methods 102, 104, 106 are always required. Method 108 is a simplified drawing of the social network communication between PNp 1610 and PFRd 1210 using a social network protocol like XMPP, in this case the PNp 1610 can login to PFRd 1210 by sending XMPP login chat messages targeted for PFRd 1210 via PSs which then forwards the login chat messages to PFRd 1210 to be handled.

Figure 1B:
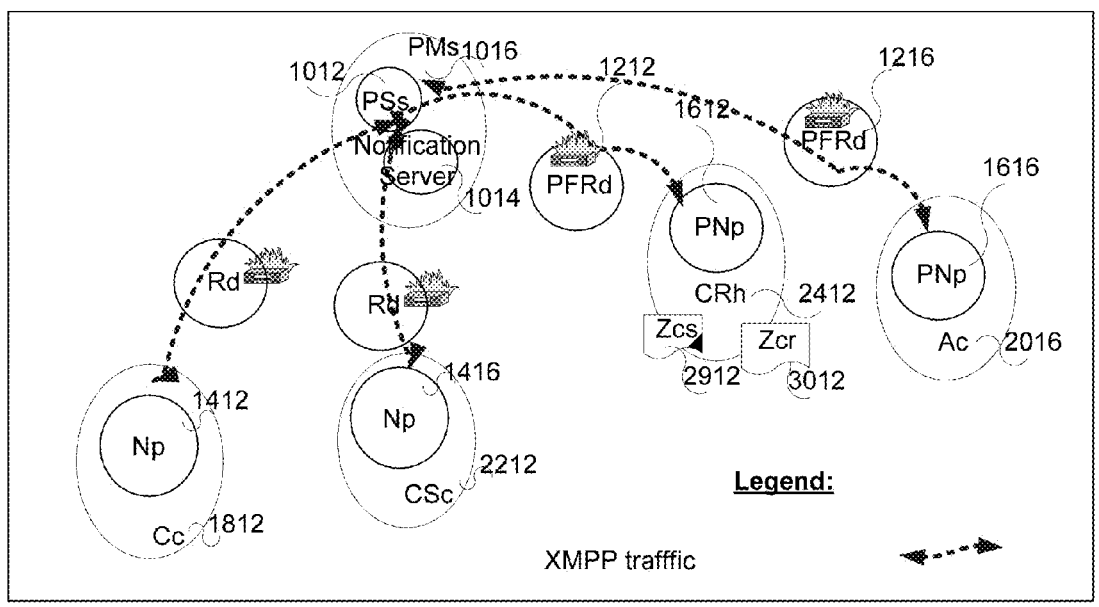
FIG. 1B shows an exemplary public multi-use server and network entities for consult workflow.

For tele-consultation service, a network system must also support additional systems and methods for the store and transfer of documents encapsulated in consult units that flow between consulters and advisors. FIG. 1B shows a preferred embodiment of network entities in the invention to support the storing and transferring of documents between peer clients.

Public-Multi-purpose-server (PMs): A single hosting central system or a centralized network of systems that supports not only the social network service for all social network clients, but may support also other services, for example the Notification service for alerting to a user of pending alerts to consults that are already submitted to the user. In an embodiment of the invention, PMs abstractly includes PSs and other well-known servers.

Also in the abstraction of the embodiment, PMs maintains a database of the workflow clients, the workflow clients' contact addresses, the workflow clients' roles and all necessary attributes to maintain operation of a social network consultation domain. It will be relevant in later detailed descriptions of the invention, how a consult from one social network consultation domain can be submitted to and returned from another social network consultation domain. For all workflow clients in the social network consultation domain, PMs is a well-known public server to all clients. FIG. 1B illustrates an exemplary of Public-Multi-purpose-servers in PMs 1016 that embodies PSs 1012 and Notification server 1014. It should be advisable to reader that the servers do not have to be collocated in a single system host—instead, they can be hosted in separate network entities that work together to provide the combined functionality of a PMs.

Consulter-client (Cc): A mobile consulter at a spoke site seeking consulting service. The consulter is mobile and is located behind multiple NAT layers. FIG. 1B illustrates Cc 1812 that combines also module Np 1412.

Consult-Submittal-station (CSs): A storage server to store submitted consults that is mobile also with the consulter at a spoke site. The storage server is mobile and is located behind multiple NAT layers. FIG. 1B illustrates CSs 2212 that combines also module Np 1416.

Consult-Resolution-hub (CRh): A storage server to store resolutions for a plurality of advisors. A CRh and its storage of resolutions can also be made available to consulters if so chosen. A CRh is a client of the social network system with public addressing mode, is stationary and always-on, is associated with a Privilege Forwarding Router device. The resolution storage associated to an advisor can be as complex as a large database or can be as simple as a resolution folder where the Zipped-consult-resolutions (see below) are stored.

Advisor-client (Ac): A specific client of the social network system that typically runs at a hub site to provide consulting service to other consulters at spoke sites. FIG. 1B illustrates Ac 2012 that combines also PNp 1612.

Zipped-consult-submittal (Zcs): A computer readable medium in an embodiment containing an assembly of data of an originally submitted consult encrypted according to consult data protection requirement as dictated by a social network consultation domain wherein the assembly comprise a copy of the originally submitted consult, wherein the data in the assembly can be fully included in the assembly or can be distributable wherein said data are only references to remote resources external to the assembly. The use of label "Zip" is only incidental as a popular replacement for "compression" in the invention description. FIG. 1*b* illustrates Zcs 2912 that is stored at CRh 2412.

Zipped-consult-resolution (Zcr): A computer readable medium in an embodiment containing an assembly of data encrypted according to consult data protection requirement as dictated by a social network consultation domain wherein the assembly comprise a copy of portion of originally submitted consult plus a plurality of copies of portion of consult advices, wherein the data in the assembly can be fully included in the assembly or can be distributable wherein said data are only references to remote resources external to the assembly. In an exemplary embodiment, various annotations added to an original Zcr by various authors in the resolution workflow are stored externally to the original Zcr, wherein only references to said annotations are stored in the original Zcr. The use of label "Zip" is only incidental as a popular replacement for "compression" in the invention description. FIG. 1B illustrates Zcr 3012 that is stored at CRh 2412.

Second Embodiment

Audio/Video/File Chat for Peer Clients of A Social Network System

Embodiments for Audio/Video/File Chat for 2 Parties Using P2P (Peer-to-Peer) Privilege Relay Channel.

Figure 2A:
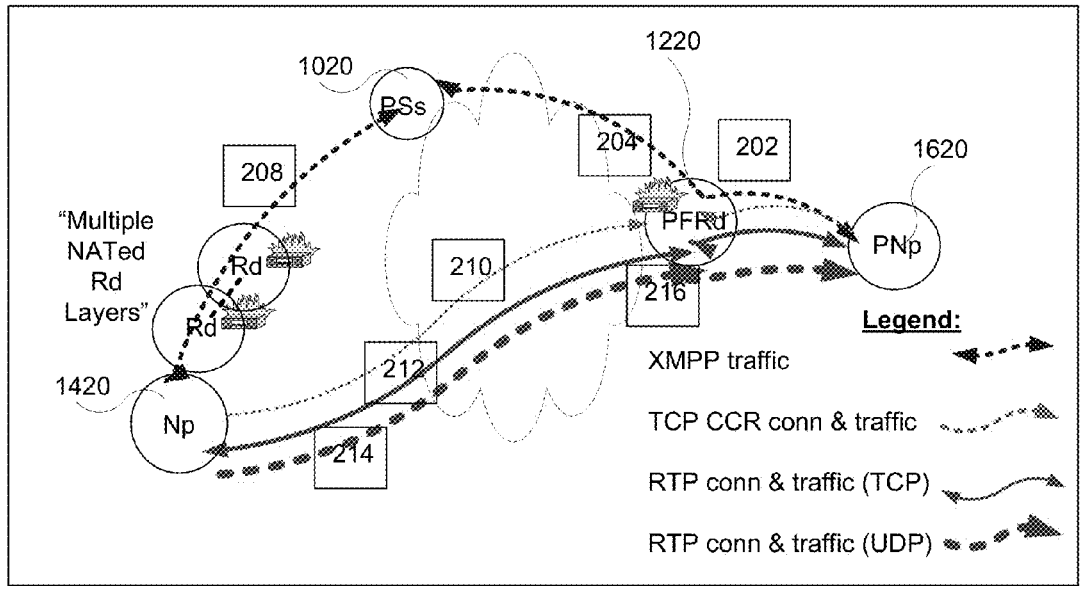
FIG. 2A shows exemplary direct video chatting/video streaming between a NATed peer (Np) and a Privilege NATed peer (PNp).
Figure 2B:
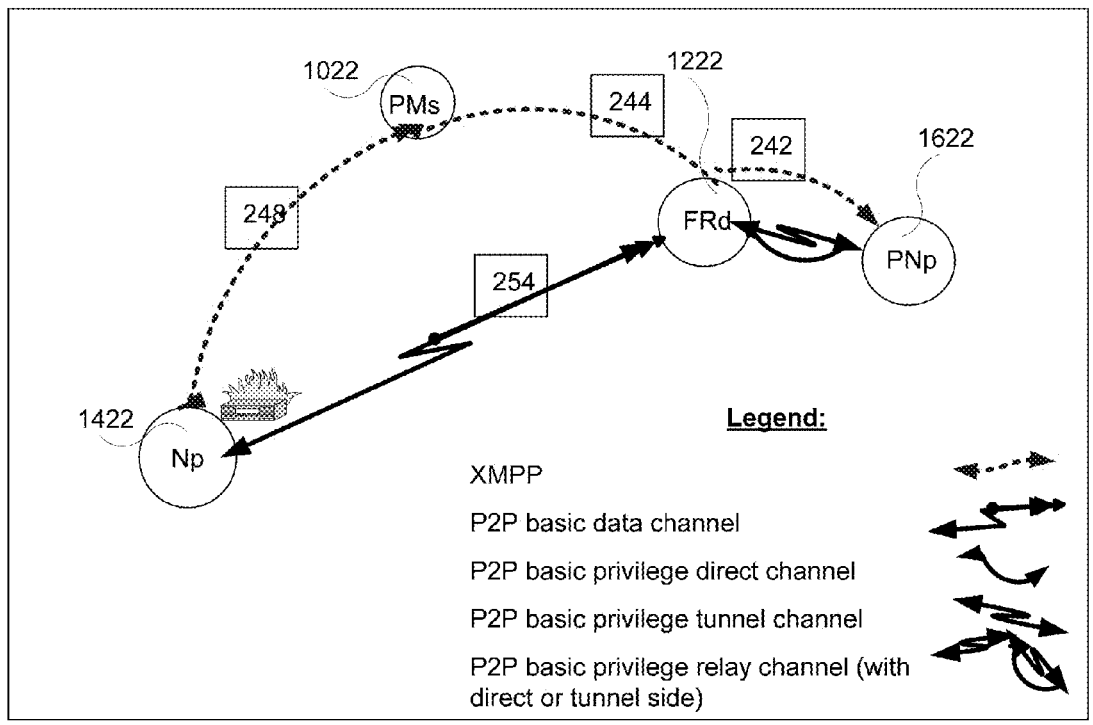
FIG. 2B shows an exemplary simplified view of FIG. 2A also for direct video chatting between a NATed (Np) and a Privilege NATed peer (PNp).

FIG. 2A and FIG. 2B illustrates a preferred embodiment of systems and methods to support an audio/video/file chat session in a social network domain administered by a PSs system, initiated by a first user interacting with a NATed-peer (Np) system to contact a second user interacting with a Privilege-NATed-peer (PNp) system, wherein all of the systems, Np, PNp, and all other supported network entities for the session that are clients of the social network domain, by default, are required to be logged in to the PSs system before additional processing.

In FIG. 2A, PSs 1020 includes instructions to employ XMPP social network protocol for peer systems to communicate between themselves as well as to and from the PMs system, and XMPP is merely an example of such social network protocols. Initially, client systems PFRd 1220, Np 1420, and PNp 1620 in the diagram all must login to the PMs system to be identified and make their presence known. Through the login methods which are not shown in the diagram, the PMs is able to identify the entity's network type of each logged-in client, and in this case, the entities associated with the peer clients are router client type, NATed client type, and privileged NATed client type in that order.

The method 202 in the diagram comprises providing the PNp to identify itself to the PFRd and subsequently, with a plurality of privilege instructions, instructing the PFRd to allocate a plurality of unused public-addressable ports (paired with the public IP of the PFRd), instructing the PFRd to forward the public-addressable ports to the equivalent private ports (paired with the private IP) of the PNp, and registering them at PFRd as being used by the PNp. In an embodiment where the PNp is locally attached directly to the LAN interface of the PFRd, and is bindable without authentication to a plurality of public-addressable ports (paired with the public IP of the PFRd) through a plurality of UPnP instructions, the privilege instructions comprise the instructions encoded in UPnP to modify the PFRd's unused public-addressable ports of its port-forward table to the equivalent unused ports paired with the private IP of the PNp. In another embodiment, where the PNp system is mobile and is external to the PFRd router, the privilege instructions comprise the instructions to register to the PFRd's VPN-server on the router's external edge, and to create a plurality of VPN tunnels linking from the PNp's equivalent unused private ports to the PFRd's VPN external edge ports, comprise also the authorization instructions for the PNp to modify the PFRd's port-forward table for the plurality of unused public-addressable ports (with the public IP of PFRd) to the equivalent VPN external edge ports paired with the private IP of the PNp through the created VPN tunnels.

The method 208 in the diagram comprises the instructions for the Np to announce to the PNp that the Np wants to initiate a video chat call to the PNp. The method 204 comprises the instructions for the PNp to communicate back to the Np that the public-addressable ports (with the public IP of the PFRd)

are available for either making connections to the PFRd using connection-oriented protocol such as TCP, or sending data directly to the PFRd using datagram-oriented protocol such as UDP.

The method 208 in the diagram comprises the instructions for the Np to announce to the PNp that the Np wants to initiate a video chat call to the PNp. The method 204 comprises the instructions for the PNp to communicate back to the Np that the plurality of public-addressable ports (with the public IP of the PFRd) remapped in method 202 are available for making chat application connections to PNp.

The methods 210, 212, 214, and 216 comprises the instructions for the Np to open and utilize in that order a plurality of connections and datagram paths to the PNp using an embodiment of protocols for 2-way video transmission such as TCP and RTSP/RTCP and RTP/UDP for video chat. Direct control/command/relaying (CCR) data between Np and PNp are sent via a TCP connection labeled CCR, audio/video data from Np is sent to PNp via a RTP/UDP datagram path; audio/video data from PNp is sent to Np via a reverse RTP/TCP connection. FIG. 2A illustrates an optimization technique of using a single TCP connection, CCR, to carry not only RTSP/RTCP traffic but also to relay proprietary commands and controls from Np to PNp and vice-versa. It is apparent to those skilled in the art that once a plurality of direct connections and direct datagram paths from a network entity having an IP endpoint behind multiple NAT layers to another network entity being one NAT layer behind a public IP endpoint, a P2P basic data channel is established for data to be sent in both directions. In FIG. 2A, the P2P basic data channel between Np 1420 and PNp 1620 is shown to comprise the TCP CCR connection, the RTP/UDP datagram path, and the RTP/TCP connection.

The pairing of unused public-addressable ports allocated by PFRd to be equivalent to unused private ports of PNp is to be regarded as illustrative rather than restrictive. Many variations of the pairing from a public-addressable port (paired with the public IP) of PFRd to a private-port (paired with the private IP) of PNp will become apparent to those skilled in the art upon review of the disclosure.

Subsequently, when the Np client wants to disconnect the video chat, the Np in an embodiment, sends the instructions comprise the XMPP disconnect message to the PNp, comprise also instructions to disconnect and release all the connections and all the private ports and all the public-addressable ports that are previously created, reserved, or used.

FIG. 2B is a simplified block diagram generalizing the same concept presented in FIG. 2A. In the diagram, method 242 in FIG. 2B, executed by PNp 1622, replaces equivalent method 202 in FIG. 2A in reserving unused public-addressable ports at PFRd 1222, checking whether PNp is one level of NAT behind PFRd so UPnP should be used or PNp is multiple levels of NAT behind PFRd so VPN tunnels should be used, executing a plurality of privilege instructions based on the results of the checking, the privilege instructions comprise creating and maintaining a control channel to the PFRd, reserving a plurality of public addressable ports on the PFRd, modifying the public forward address table of the PFRd to forward the reserved public addressable ports (with public IP address of PFRd) to the PNp's private addressable ports (with private IP address of PNp), managing effectively a plurality of P2P basic privilege data channels (that are established on as needed basis) to communicate between the PNp peer and the PFRd peer. Method 244 is equivalent to method 204, and 246 to 208. Method 248 in FIG. 2A comprises methods 210, 212, 214 and 216 in FIG. 2A, also combines instructions for Np 1422 chatting with PFRd 1222 to retrieve from the PFRd a registered list of public addressable ports (with public IP of PFRd 1222) for communicating to the PNp, establishing a plurality of connections and a plurality of data paths based on the registered list to create a P2P basic data channel between the Np peer and the PFRd peer that is mapped and relayed at PFRd peer location to one of the plurality of P2P basic privilege data channels between the PFRd peer and the PNp peer. It is apparent to those skilled in the art that once the three peers Np, PFRd and PNp agree to a plurality of connections and datagram paths to be created and built by the network entity systems with methods as embodied in FIG. 2B, a P2P basic data relay channel is established for data to be sent in both directions between the Np to the PNp via the relay PFRd.

According to another embodiment to support audio/video/text/file chat between a Privileged-NATed-peer (PNp) and a Privileged-NATed-peer (PNp), it is apparent to those skilled in the art that since both PNp peers can authorize their associated routers to reserve, bind, and redirect to themselves a plurality of public-addressable ports, a P2P basic data channel between the 2 peers is a simple matter to be constructed.

According to another embodiment to support audio/video/text/file chat between 2 peers, a second NATed-peer and a third NATed-peer, it is apparent to those skilled in the art that a relay agent associated to a public router is needed. Reference to the relay agent is available in the document "NAT Traversal in Peer-to-Peer Architecture" document.

Figure 2C:
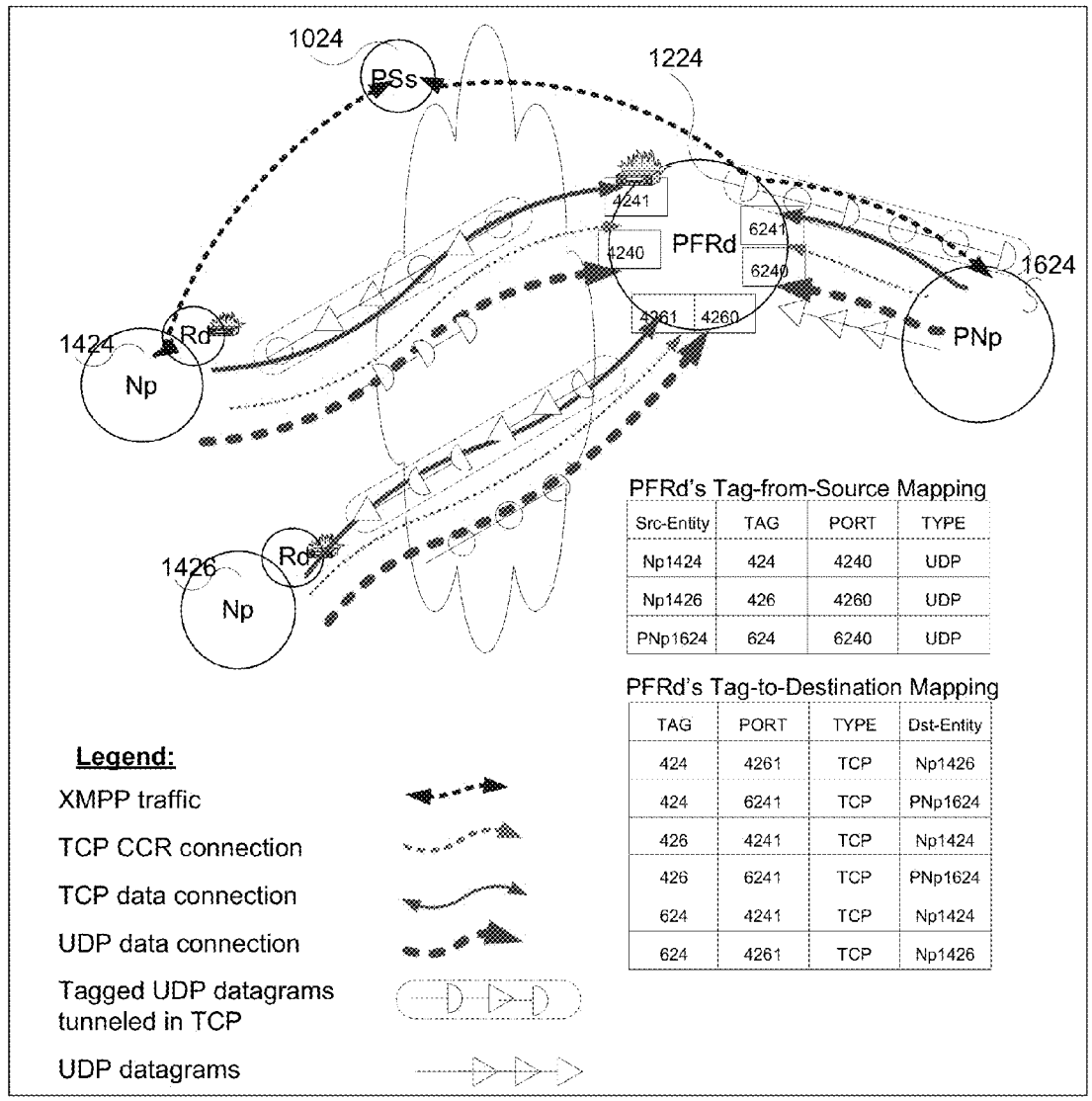
FIG. 2C shows an exemplary 3-way video conferencing between 2 NATed peers, Np1, Np2 and a Privilege NATed peer PNp.
Figure 2D:
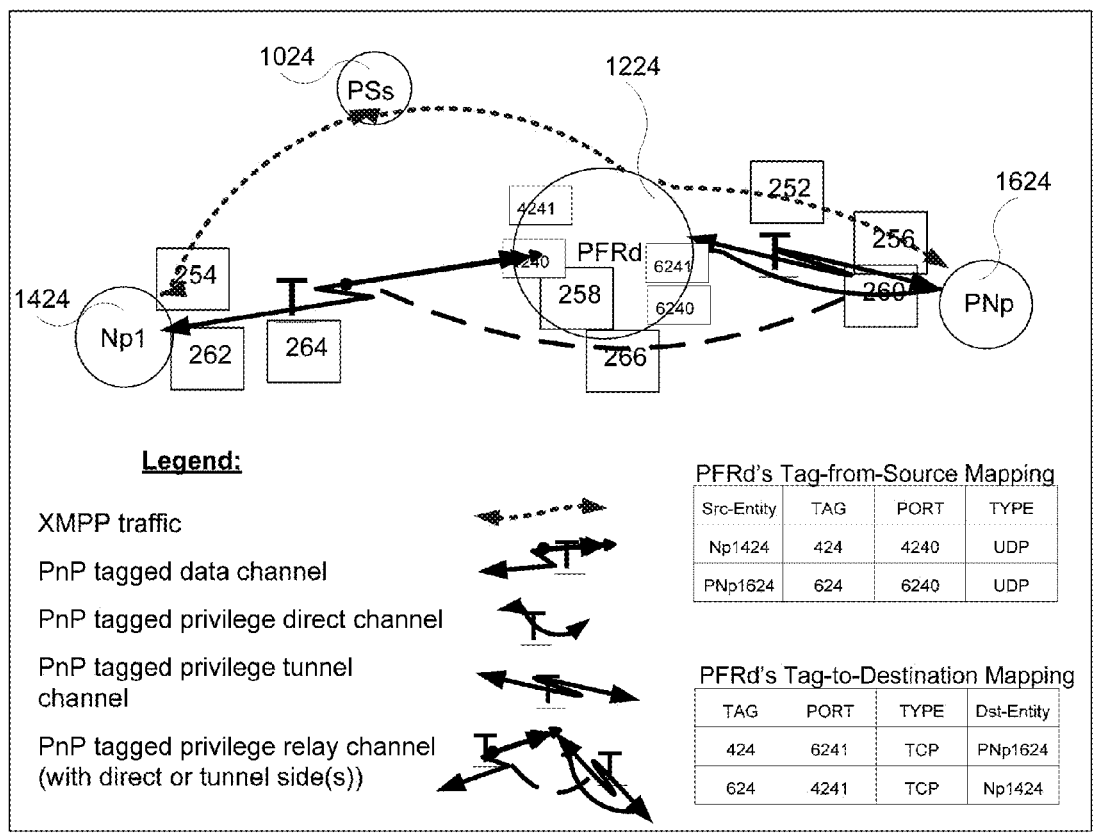
FIG. 2D shows a simplified view of FIG. 2C for video chatting between 2 peers, Np1 and PNp, using peer-multiple-peer (n-way) tagged privilege relay channel.
Figure 2E:
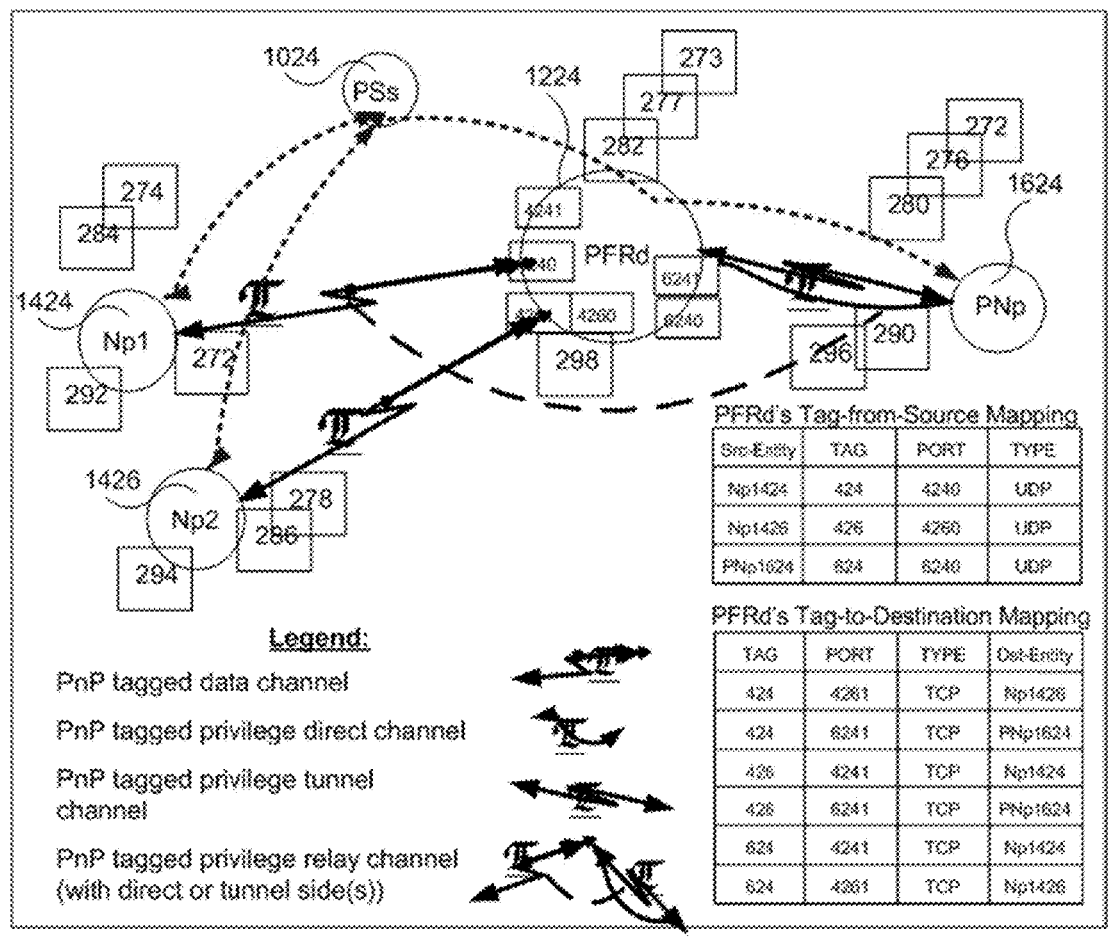
FIG. 2E shows a simplified view of FIG. 2C for video conferencing between 3 peers, Np1, Np2, and PNp, using peer-multiple-peer (n-way) tagged privilege relay channel.

Embodiments for Audio/Video/File Conference for Multiple Parties Using PnP (Peer-to-Multiple-Peer) Tagged Relay Channel FIGS. 2A and 2B illustrate a preferred embodiment of an interactive direct audio/video communication between a PNp peer and a Np peer that is common for peer-to-peer (P2P) for a direct teleconsult session between a consulter and an advisor through a non-advanced PFRd. In a few cases where video conferencing between multiple users is required, the non-advanced PFRd in FIGS. 2A-2B would not be sufficient to support peer-to-multiple-peer (PnP) video conferences. In this case, the peers require higher support of multi-party conference by switching, either automatically based on a cost-based pre-programmed program module or manually based on a preferred selection by the conference controlled participant, to a new advanced PFRd that supports PnP tagged relay channel. Such new switching is illustrated in FIGS. 2C-2E below wherein the figures illustrate an embodiment of systems and methods to support a video conference session in a social network domain administered by a PSs system for 3 peers, 2 normal peers Np1, Np2, and a privilege peer PNp, relayed by a privilege forwarding advanced router device PFRd, wherein the video conference is implemented by a conference bridge that duplicates audio/video signals from participants other than a targeted participant and sends said duplications to each targeted conference participant. Due to the complexity of supporting economically the ability of video conferencing from a controlled party to a few participants or to a large plurality of audience and the quality of audio and video to each tributary channel of the conference bridging network, it is important that an implementation of the video conference embodiment of the invention shall include the support of a plurality of advanced and non-advanced PFRds per each user per each PNp agent system that said user might access to, first to guarantee the availability of bandwidth from a given PFRd for high quality of video streaming, and second, to guarantee the availability of high quality audio/video conferencing relay channels that are only available with the advanced PFRds.

Figure 9:
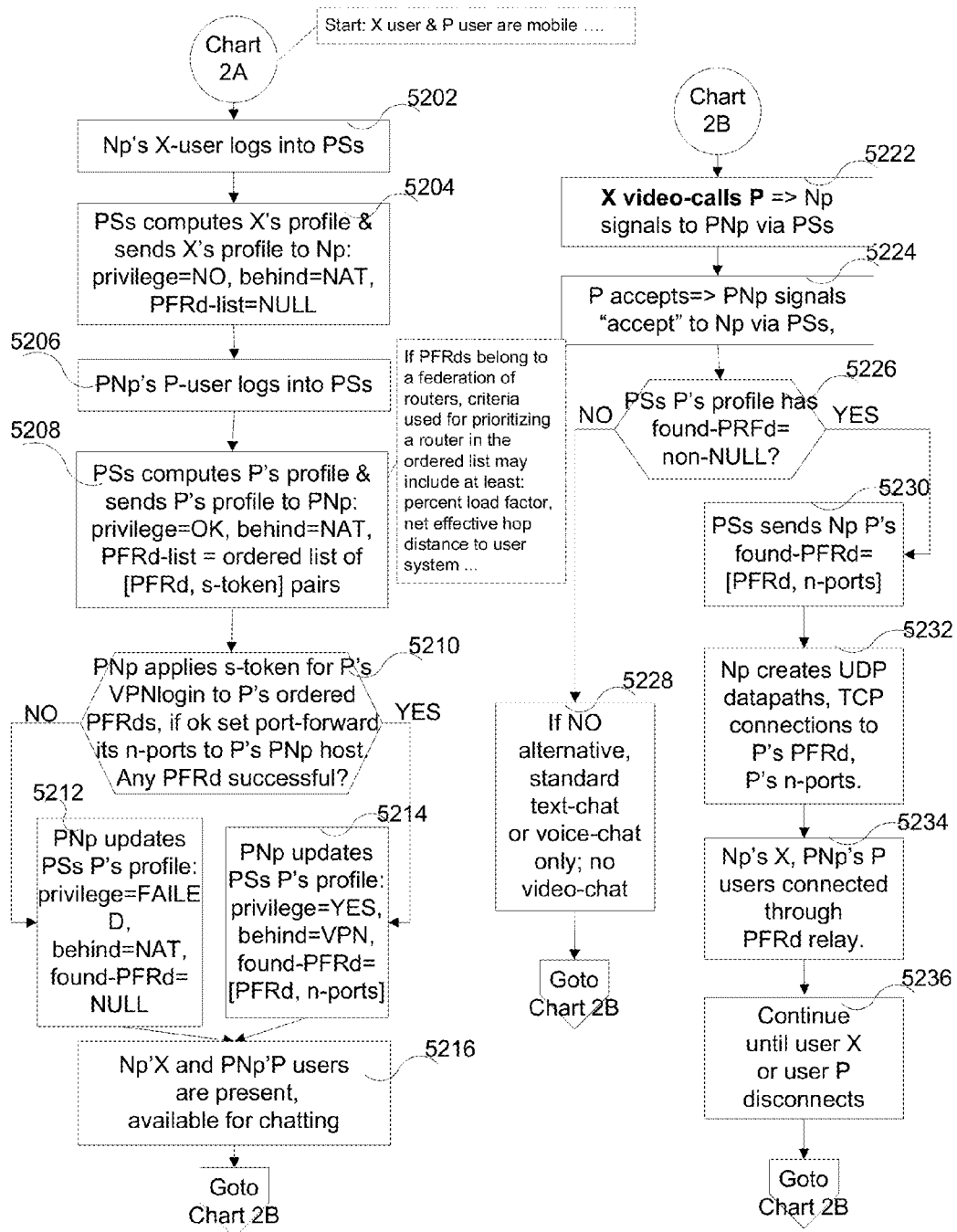
FIG. 9 shows an exemplary flowchart to connect Np to PNp peers.

It is apparent to those skilled in the art that in the case that the management of a plurality of advanced and non-advanced PFRds per user is required, also referred in FIG. 9 of the invention as the management of a federation of PFRds, said management always includes the health (up/down) status, the percent loading factor status, the net effective relative distance in number of hops calculated from a dynamic topology scan to collect the location of network entities, and the configuration privilege for N-way video conference before returning a preferred ordered list of PFRds for a peer client to use. It is also apparent that in the case a user is not already on an advanced PFRds supporting PnP tagged privilege relay channel for 2 peers, and a 3-way or N-way relay channel is needed for conferencing more than 2 participants, said user will need to switch out of said non-advanced PFRd and into an advanced PFRd in order for said advanced PFRd to bridge said N-way conferencing.

FIG. 2C illustrates in detail graphics the formation of CCR, UDP and TCP connections from each participant in the conference call, and incoming packets that arrive from the formation of a first table and a second table in the PFRd, wherein the first table provides the Tag-From-Source (TFS) mapping to identify a source network entity of incoming packets of a video stream, wherein the second table provides the Tag-To-Destination (TTD) mapping to enable the forwarding of the packets to destination network entities in a video conference with multiple users wherein each network entity is a user agent for each user. In FIG. 2C, during video conference, audio/video stream packets from Np1 1424 and packets from Np2 1426 are routed to PNp 1624, audio/video packets from Np2 1426 and from PNp 1624 are routed to Np1 1424, audio/video packets from Np1 1424 and from PNp 1624 are routed to Np1 1424. Without any modification or filtering to the incoming packets, it is clear that the TTD mapping table will generate for output a total bandwidth at about twice (2×) the sum of total input bandwidth. A few techniques for optimizing the total output bandwidth are also presented at the end of this section.

FIGS. 2D-2E are two simplified block diagrams generalizing the same concept presented in FIG. 2C with the same identification for the network entities, for ease of comparison. FIG. 2D illustrates 2 peers voice conference using PnP tagged privilege relay channel (with direct or tunnel side channel). FIG. 2E illustrates 3 peers voice conference using PnP tagged privilege relay channel (with direct or tunnel side channel).

In FIG. 2D, method 252 provides instructions for PNp to request tagged video chat to Np1 through PFRd device as the device is public addressable. In method 254, Np1 accepts request from PNp and opens a CCR connection to PFRd. In method 256, with privilege instructions, PNp sends requests to PFRd to create a conference bridge for 2 peers. Method 257 at PFRd reserves open ports and creates two mapping tables for the conference bridge as shown in FIG. 2*d*. for the TFS mapping table and the TTD mapping table. Method 258 at PNp, and method 259 at Np1 form the UDP data path and TCP connection with assigned tags for each connection according to the mapping tables. Method 260 at PNp, method 262 at Np1, and method 264 cooperate to continuously send tagged input audio/video stream on UDP data path, and decode audio/video output stream on TCP connection.

It is apparent to those skilled in the art that once the three peers Np, PFRd and PNp agree to a plurality of connections and datagram paths to be created and built by the network entity systems with methods as embodied in FIG. 2C and FIG. 2D, a (2-way) P2P basic data relay channel is established for data to be sent in both directions between the Np to the PNp via the relay PFRd. Moreover, since the channel uses tagging mechanism for de-multiplexing incoming data into outgoing data, the data relay channel is applicable also as a peer-to-multiple-peer (PnP) N-way data relay channel.

Between Np1, Np2, and PNp Using PnP Tagged Privilege Relay Channel

In FIG. 2E, it is assumed PNp 1624, PFRd 1224, Np1 are already connected in a 1st 2-way PnP tagged privilege relay channel. Method 272, 273, 274 for PNp, PFRd, Np1 in that order execute PNp's request to put the tagged privilege relay channel on hold. As such PNp's UDP data path on port 6240 and TCP connection on port 6241 are free for making video connection. Method 276, 277, 278 for PNp, Np2, and PFRd in that order implement PNp's request to create a 2nd 2-way PnP tagged privilege relay channel from PNp to Np2. Method 280, 282, 284, 286 for PNp, Np1, Np2, and PFRd in that order cooperate to implement PNp's request to join Np1 to the 2nd 2-way PnP tagged privilege relay channel in order to combine the 1st 2-way tagged privilege relay channel and the 2nd 2-way PnP tagged privilege relay channel into a 3-way tagged privilege relay channel. Two tables TFS mapping and TTD mapping in FIG. 2E illustrate the tags and routings of the conference bridge of the 3-way relay channel in PFRd. Method 296 and method 298 at PNp and PFRd execute PNp's request to break down the video conference.

It is apparent to those skilled in the art that once the four peers Np1, Np2, PFRd and PNp agree to a plurality of connections and datagram paths to be created and built by the network entity systems with methods as embodied in FIG. 2E, an N-way peer-to-multiple-peer (PnP) tagged privilege relay channel is established for data to be sent in all directions between all peers via the relay PFRd. It is apparent that since only PNp party has the privilege to modify the conference bridge circuit, all requests impacting the conference bridge (e.g. inviting) from other participants in the conference shall be sent to PNp party to be executed.

Not shown in FIGS. 2C-2E is the handling at a peer's local host system of the audio component of each audio/video stream at a peer entity, wherein the audio component must be stripped off from each incoming audio/video stream, sent to a local audio mixer, mixed with all other incoming audio components, mixed also with the local audio source of the local host, filtered away any locally echoed audio component of the local audio source, before outputting to the speaker of the local host system.

Also not shown in FIGS. 2C-2E are several optimization techniques applicable in reducing the total output bandwidth at a PFRd: (a) Allow either manual or auto detection of a participant who is momentarily the speaker or the attention-getter of the video conference, (b) In the combined video stream tunneled in TCP connection returned to a peer entity, for the speaker's or the attention-getter's video stream, maintain the video resolution for the stream to be the same or as close as possible to the stream's input resolution, while reducing the resolutions for the video streams of all other participants, wherein the application of H.264/SVC scalar video coding standards will be useful for the selective reduction of video resolution, (c) Support within PFRd audio mixer circuits to split audio component from incoming audio/video streams and premix all needed audio components targeted for a destination entity into one combined audio component before sending off to a destination entity. Any of the optimization techniques, if implemented, will incur higher cost to the network system in order to support video conferencing.

Third Embodiment

Data Capture by Consulter-Client (Cc) to Database

Figure 3:
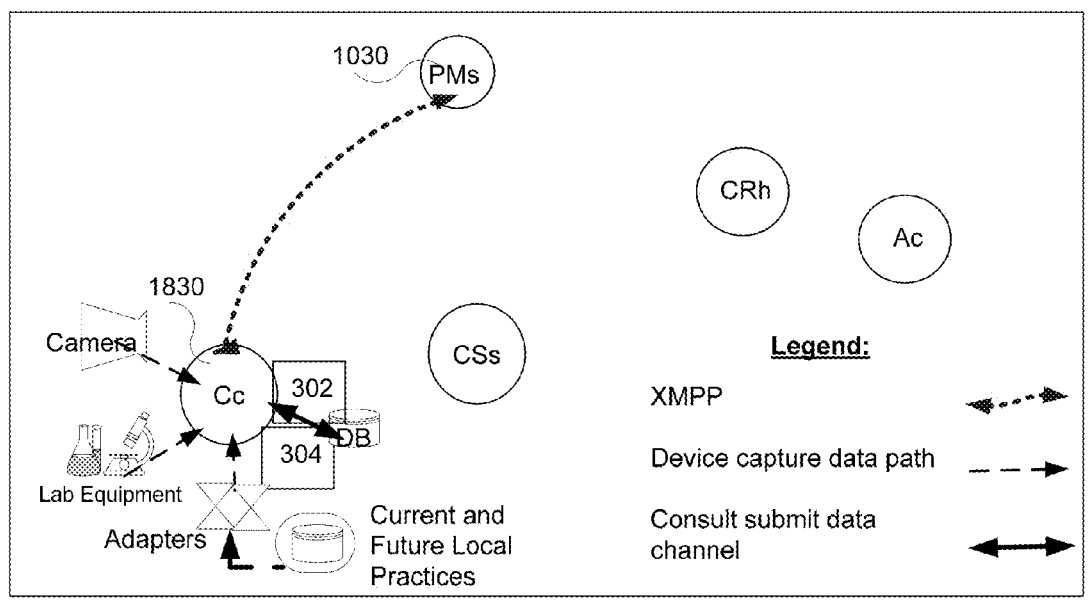
FIG. 3 shows an exemplary data capture by a consulter-client to a local database.

FIG. 3 illustrates an embodiment of systems and methods for a beginning stage of a consult workflow to submit and resolve a consult in a social network domain administered by a PMs system, wherein a Cc client system of the social network domain, by default, is required to be logged in to the PMs system before additional processing, wherein in the stage, a new case is created, capture data is input into the case after being checked for integrity and the result is stored in a database wherein the new case may or may not be later translated into a consult to be used for a submission.

Consulter-client Cc 1830 in the illustrated embodiment includes a set of instructions comprise providing a user interface to allow a plurality of interactions between a user and the computer system, the interactions comprise logging into the social network domain of logging into the database shown in method 302, comprise other instructions of method 304 that include creating a new empty case, capturing direct data into the case from illustrated devices such as camera and lab equipment, capturing monitored data from monitoring equipment, activating a plurality of adaptive agent modules that interfaces to a plurality of current and future local practice systems to input data indirectly from the adaptive agents.

Fourth Embodiment

Workflow to Resolve Consultations Stored at an Always-On-Line Consult-Submittal-Station (CSs)

Figure 4A:
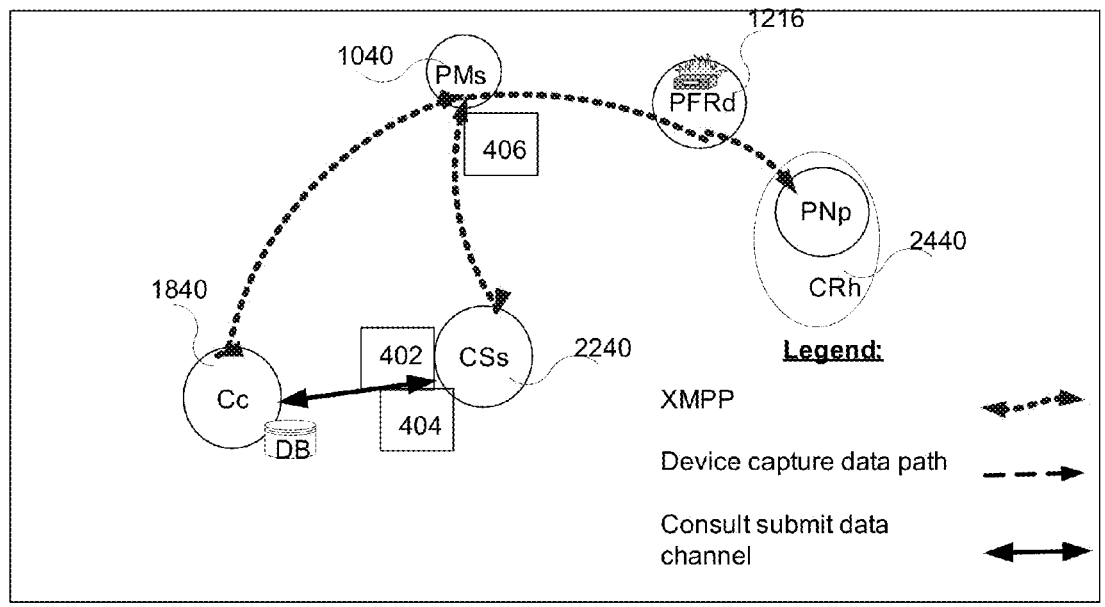
FIG. 4A shows an exemplary consult submit flow for an always-online 24/7 consulter submit station (CSs).
Figure 4B:
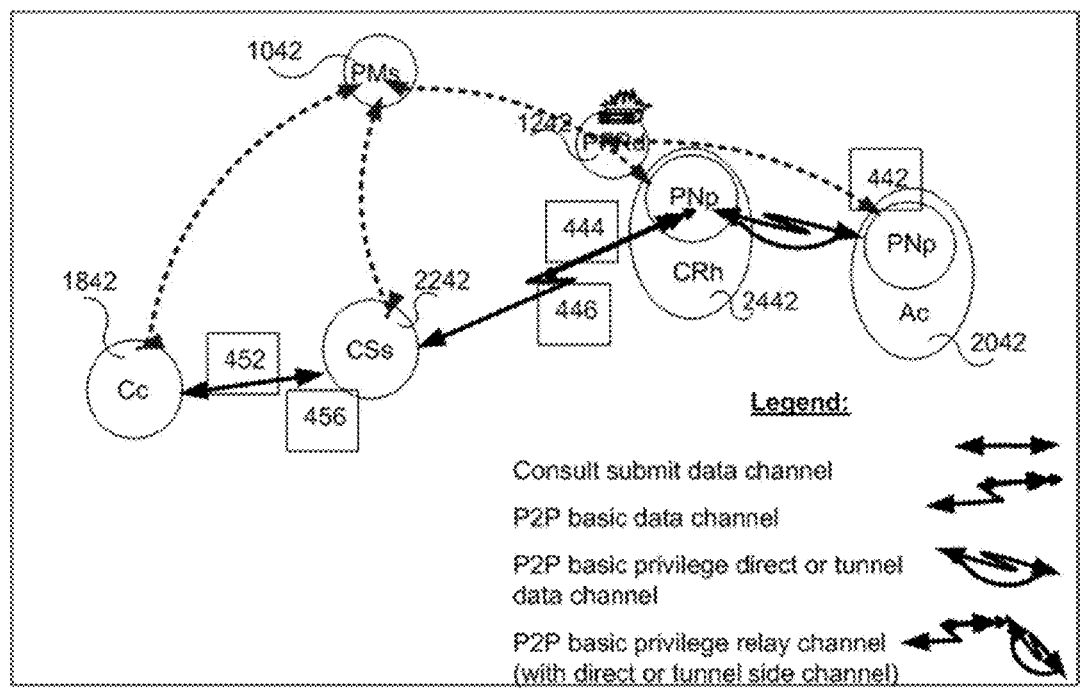
FIG. 4B shows an exemplary consult review & return flow for an always-online 24/7 consulter submit station (CSs).

FIG. 4A and FIG. 4B illustrates a preferred embodiment of systems and methods for a workflow to submit and resolve a consult in a social network domain administered by a PMs system, submitted by a consulter interacting with a Consult-client (Cc) system and resolved by an advisor interacting with an Advisor-client (Ac) system, wherein the consult during the submission is stored at an always-on-line Consult-Submittal-station (CSs) server, wherein all of the systems, Cc, Ac, CSs, and all other supported network entities for the workflow that are clients of the social network domain, by default, are required to be logged in to the PMs system before additional processing.

FIG. 4*a* illustrates a preferred embodiment of systems and methods to submit the case in FIG. 3*a* after it is captured, the case is changed into a consult, the consult is submitted to a plurality of allowed advisors and is stored at a server wherein the consult can be accessed locally and remotely over the internet link and updated directly during the server's uptime, wherein the server is always powered up and is kept on-line, except for scheduled down time for maintenance.

Cc 1840 includes a set of instructions comprising providing a user interface to allow a plurality of interactions between a user and the computer system, the interactions comprise method 402 to login to CSs 2240 and method 404 to select a case that is created and captured in a database and to select a plurality of allowed and configured advisors to review and resolve the case, convert the case into a consult stored at CSs 2240, comprise also method 406 including submitting the consult to the advisors, posting notification messages to PMs 1040 to alert the advisors of the submitting of the consult.

FIG. 4B illustrates a preferred embodiment of systems and methods for a plurality of actions to resolve a consult submitted by a consulter to a plurality of recipient advisors wherein the submitted consult is stored in an always-online server, wherein the recipient advisors are required to access the server using a P2P basic privilege relay channel as described according to the embodiment of FIG. 2A, wherein a plurality of first interactions between the consulter and a first one of a plurality of the recipient advisors and a plurality of second interactions between the consulter and a second one of a plurality of the recipient advisors are different only in contents but not in methods.

In FIG. 4B, Advisor-client Ac 2042 in the illustrated embodiment includes a set of instructions comprising providing a user interface to allow a plurality of interactions between a user and the computer system, the interactions result in receiving and consuming the notifications and alerts, executing in method 442 a plurality of privilege instructions to login to CRh 2442, configuring a plurality of P2P basic privilege data channels (to be established on an as needed basis), logging into CSs 2242 in method 444 to review the submitted consult, executing method 446 including instructions comprise annotating into the submit consult a consult advice with supporting attributes as a plurality of snapshots of submitted materials to be stored in CSs 2242 and extracting a copy of the consult advice including the supporting attributes to be stored at CRh 2442, notifying the consulter of the availability of the consult advice.

In FIG. 4B, CSs 2242 server in the illustrated embodiment includes a set of instructions comprising providing a log-in mechanism for storing log-in information of a plurality of users, each user is coupled with a plurality of roles defining the user's role-based access and behavior rules, authorizing an embodiment of access and behavior rules coupled for a user a set of instructions comprising identifying a consult with a plurality of consult advices, delegating the CSs to extract, zipping and forwarding a copy of the consult with the accessible consult advices to a public server designated by the user.

In FIG. 4B, Consulter client Cc 1842 in the illustrated embodiment includes a set of instructions comprising providing a user interface to allow a plurality of interactions between a user and the computer system, the interactions result in receiving and consuming the notifications and alerts, logging into CSs 2242 in method 452 to review the consult advice annotation, determining for resubmitting the consult in a plurality of iterations and resubmitting the consult if so determined, determining for reaching resolved state of the consult with the advisor and taking action if so determined in method 456 including instructions comprise setting to resolved state of the consult advice to the advisor and synchronize-updating to resolved state also to the consult advice at CRh 2442, determining for closing the consult after reaching resolved state to the all submitted advisors, and if so determined, executing method 458 including instructions comprising setting to closed state of submitted consult and synchronize-updating to closed state also to all the consult advice annotations having been stored at CRh 2442 in connection to the submitted consult.

In FIG. 4B, CRh 2442 server in the illustrated embodiment includes a set of instructions comprising providing a log-in mechanism for storing log-in information of a plurality of users, each user is accessible to the CRh with a plurality of roles defining the user's role-based access and behavior rules, authorizing an embodiment of access and behavior rules coupled for a user a set of instructions comprising receiving a zipped Zcr record into local storage from an agent process delegated by the accessible user.

Multiple iterations of FIG. 4B between a consulter party and a recipient advisor party are expected in order to resolve the submitted consult to a satisfactory level, agreeable to both the consulter party and the recipient advisor party, until the submitted consult reaches resolved state between the consulter party and the recipient advisor party.

Fifth Embodiment

Workflow Resolve Consults Stored at Off-on, not-Always-on-Line Consult-Submittal-Station (CSs)

Figure 5A:
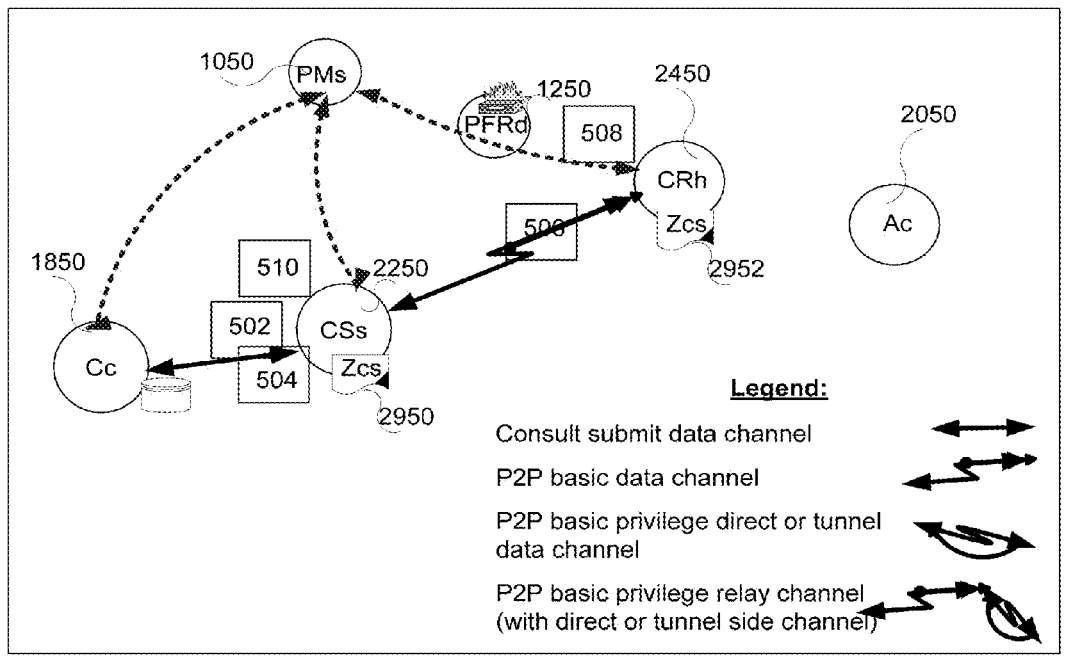
FIG. 5A shows an exemplary consult submit flow for an on-off consulter submit station (CSs).
Figure 5B:
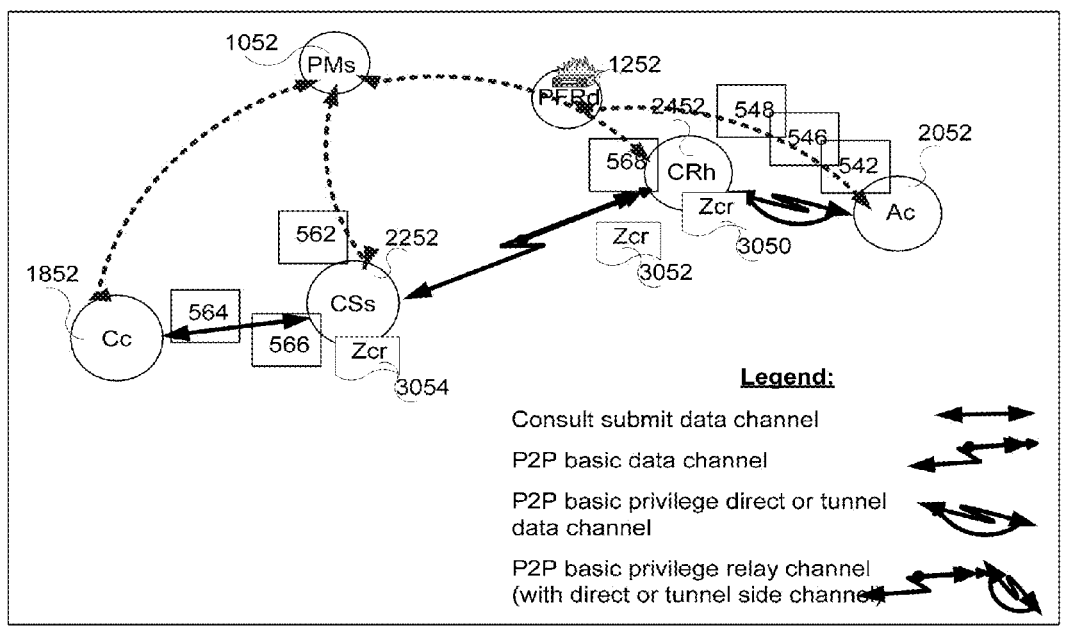
FIG. 5B shows an exemplary consult review & return flow for an on-off consulter submit station (CSs).

FIG. 5A and FIG. 5B illustrate an embodiment of systems and methods for a workflow to submit and resolve a consult in a social network domain administered by a PMs system, submitted by a consulter interacting with a Consult-client (Cc) system and advised by an advisor interacting with an Advisor-client (Ac) system, wherein the consult during the submission is stored at a Consult-Submittal-station (CSs) server that can be turned off-on, that is not always-on-line, wherein all of the systems, Cc, Ac, CSs, and all other supported network entities for the workflow that are clients of the social network domain, by default, are required to be logged in to the PMs system before additional processing. In real life situation, the embodiment is very common if and when a single computing equipment that is used to host both a Cc system and a CSs server needs to be powered off to be mobile to be moved to a different location.

FIG. 5A illustrates an embodiment of systems and methods to submit the case in FIG. 3A after it is captured, the case is changed into a consult stored at a local server that is not always-on-line for remote access, the consult is submitted to a plurality of allowed advisors, a copy of the submitted consult is maintained at an always-on-line public server wherein the copy can be annotated in a plurality of consult advices, one by each of the allowed advisors.

In FIG. 5A, Cc 1850 includes a set of instructions comprising providing a user interface to allow a plurality of interactions between a user and the computer system, the interactions comprise method 502 to login to CSs 2250, comprise method 504 that include a set of instructions comprising selecting a case that is created and captured in a database, selecting a plurality of allowed and configured advisors to review and resolve the case, converting the case into multiple consults submitted to the advisors, each consult suitable for an advisor's practice in a consult network domain, storing the consults at CSs 2250, comprise method 506 that includes a set of instructions comprising delegating CSs 2250 the task of forwarding the submitted consults to an identified remote server which may be public and suitable for the advisors.

In FIG. 5A, CSs 2250 server in the illustrated embodiment includes a set of instructions comprising providing a log-in mechanism for storing log-in information of a plurality of users, each user is coupled with a plurality of roles defining the user's role-based access and behavior rules, authorizing an embodiment of access and behavior rules coupled for a user a set of instructions comprising identifying a consult with a plurality of consult advices, delegating the CSs to extract, zip and forward a copy of the consult with the accessible consult advices to a public server designated by the user. Being delegated by instructions from Cc 1850, CSs 2250 executes method 506 comprising zipping the consult into a Zcr record suitable for interruptable file streaming, starting file-streaming the Zcr record to the identified remote public server as CRh 2450. If CSs 2250 is powered off or goes off-line while file streaming of the Zcr in method 506 is not completed, the file streaming will resume also by instructions of method 506 when CSs is powered back and goes on-line again. At completion of method 506, CSs 2250 executes a set of instructions comprising method 508 including posting notification messages to PMs 1050 to alert the advisors of the submit completion of the consult.

In FIG. 5A, CRh 2450 server in the illustrated embodiment includes a set of instructions comprising providing a log-in mechanism for storing log-in information of a plurality of users, each user is accessible to the CRh with a plurality of roles defining the user's role-based access and behavior rules, authorizing an embodiment of access and behavior rules coupled for a user a set of instructions comprising delegating local agents in the CRh a plurality of missions including extracting, zipping and forwarding a plurality of copies of consults and consult advices accessible by the embodiment of rules to a public server designated by the accessible user, comprising receiving a zipped Zcr record into local storage from a agent process delegated by the accessible user.

FIG. 5B illustrates an embodiment of systems and methods for a plurality of actions to resolve a consult submitted by a consulter to a plurality of recipient advisors wherein the submitted consult is stored in a local server that is not always-on-line for remote access, wherein a copy of the submitted consult will be maintained at a public server to be reviewed and annotated with a plurality of consult advices, one by each of the allowed advisors, wherein a plurality of first interactions between the consulter and a first one of a plurality of the recipient advisors and a plurality of second interactions between the consulter and a second one of a plurality of the recipient advisors are different only in contents but not in methods.

In FIG. 5B, Advisor-client Ac 2052 in the illustrated embodiment includes a set of instructions comprising providing a user interface to allow a plurality of interactions between a user and the computer system, the interactions result in receiving and consuming the notifications and alerts, executing in method 542 a plurality of privilege instructions to log in to CRh 2452, configuring a plurality of P2P basic privilege data channels (to be established on an as needed basis), executing method 546 including instructions comprise opening and viewing the submitted Zcr 3050 record, further annotating the Zcr 3050 to include a consult advice with supporting attributes as a plurality of snapshots of submitted materials to be stored locally in CRh 2452, delegating CRh 2452 the task of returning the consult advice of the submitted Zcr back to the submitting system, CSs 2252 whenever it comes on-line. CRh 2452 executes method 548 comprising zipping the consult advice annotated to Zcr 3050 into a new Zcr record, Zcr 3052, suitable for file-streaming, determining if CSs 2250 is not online and if so determined, waiting until CSs 2252 to come on-line to stream the Zcr to the consulter, determining if CSs 2252 is online and if so determined, starting streaming the Zcr 3052 to the CSs. Furthermore, at the end of file streaming of the Zcr, CRh 2452 executes also instructions in method 548 comprising notifying the consulter of the availability of the consult advice in the streamed Zcr.

In FIG. 5B, CSs 2252 server in the illustrated embodiment includes a set of instructions comprising providing a log-in mechanism for storing log-in information of a plurality of users, each user is coupled with a plurality of roles defining the user's role-based access and behavior rules wherein the user is associated to an user, or is associated to a computer system serving as an agent for the user, executes instructions in method 562 to accept a file-streaming of Zcr record from CRh 2452 of Zcr 3052 and process the file-streaming to create Zcr 3054 record within the CSs 2252 system.

In FIG. 5B, Consult-client Cc 1852 in the illustrated embodiment includes a set of instructions comprising providing a user interface to allow a plurality of interactions between a user and the computer system, the interactions result in receiving and consuming the notifications and alerts, logging into CSs 2252, executing method 564 including instructions comprising opening and matching the Zcr record with a submitted consult that the Zcr correlates, importing the returned Zcr 3054 record and the returned consult advice included in the Zcr record into the correlated submitted consult into CSs server, determining for resubmitting the consult in a plurality of iterations and resubmitting the consult if so determined, determining for reaching resolved state of the consult with the advisor and taking action if so determined in method 566 including instructions comprise setting to resolved state of the consult advice to the advisor and synchronize-updating to resolved state also to the consult advice at CRh 2452, determining for closing the consult after reaching resolved state to the all submitted advisors, and if so determined, executing method 5688 including instructions comprise setting to closed state of submitted consult and synchronize-updating to closed state also to all the consult advice annotations having been stored at CRh 2452 in connection to the submitted consult.

Sixth Embodiment

Mobile Consulter with Static or Mobile Advisor

Figure 6A:
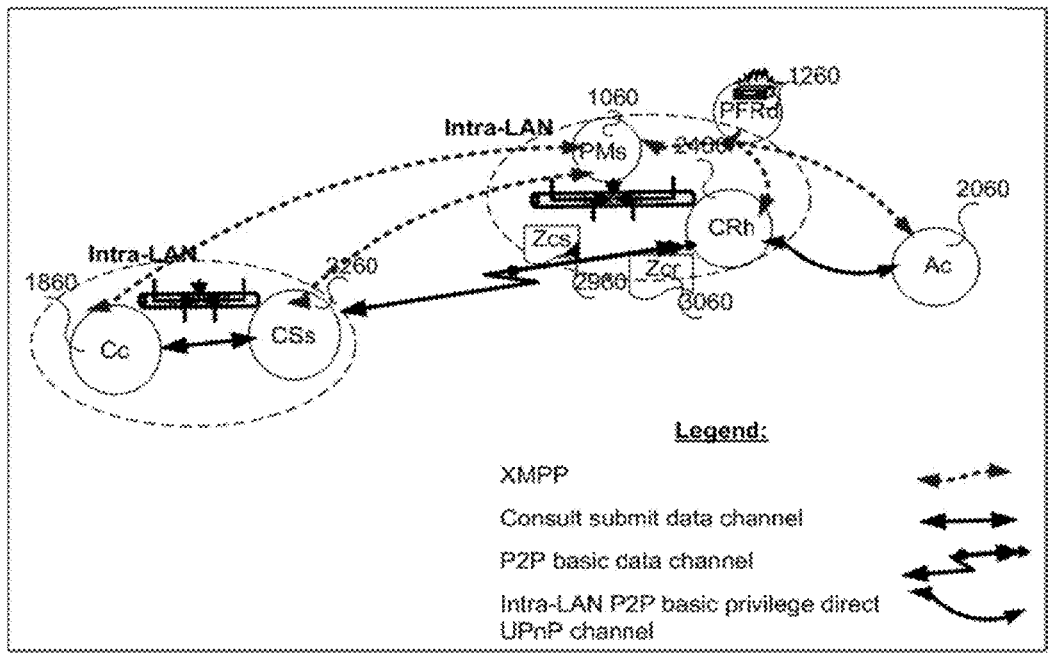
FIGS. 6A and 6B illustrate two embodiments of systems and methods for a workflow to submit and resolve a consult in a social network between a mobile consulter and an advisor that can be static or mobile.

FIG. 6A illustrates an exemplary compact embodiment of systems and methods of a 1st social network consult configuration to support teleconsulting between a mobile consulter and a stationary advisor.

In FIG. 6A, for ease of management and security, all public addressable network entities are physically located as entities linked within sub-segments of a local area network, or Intra-LAN residency wherein PMs 1060 and CRh 2460 are connected behind the same PFRd 1260 and are publicly addressable via public ports on the PFRd. Herein, while a consulter is a mobile user of both Cc 1860 and CSs 2260 systems, an advisor is stationary and is serviced by Ac 2060 which is locally attached at a local sub-segment PFRd 1260.

Figure 6B:
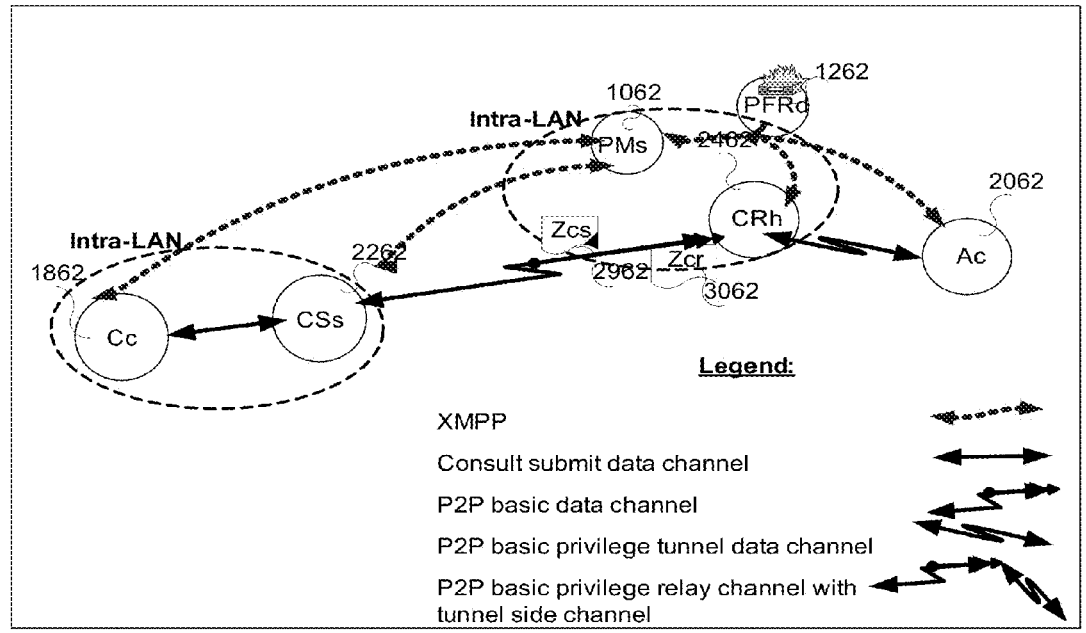

FIG. 6B illustrates an exemplary compact embodiment of systems and methods of a 2nd social network consult configuration to support teleconsulting between a mobile consulter and a mobile advisor.

Similar to FIG. 6A, FIG. 6B also illustrates Intra-LAN residency of all public addressable network entities wherein PMs 1062 and CRh 2462 are connected behind the same PFRd 1262. Herein, while a consulter is a mobile user of both Cc 1862 and CSs 2262 systems, an advisor is mobile and is serviced by Ac 2062 through a P2P basic privilege data channel connected to PFRd 1262.

Seventh Embodiment Group

Figure 7:
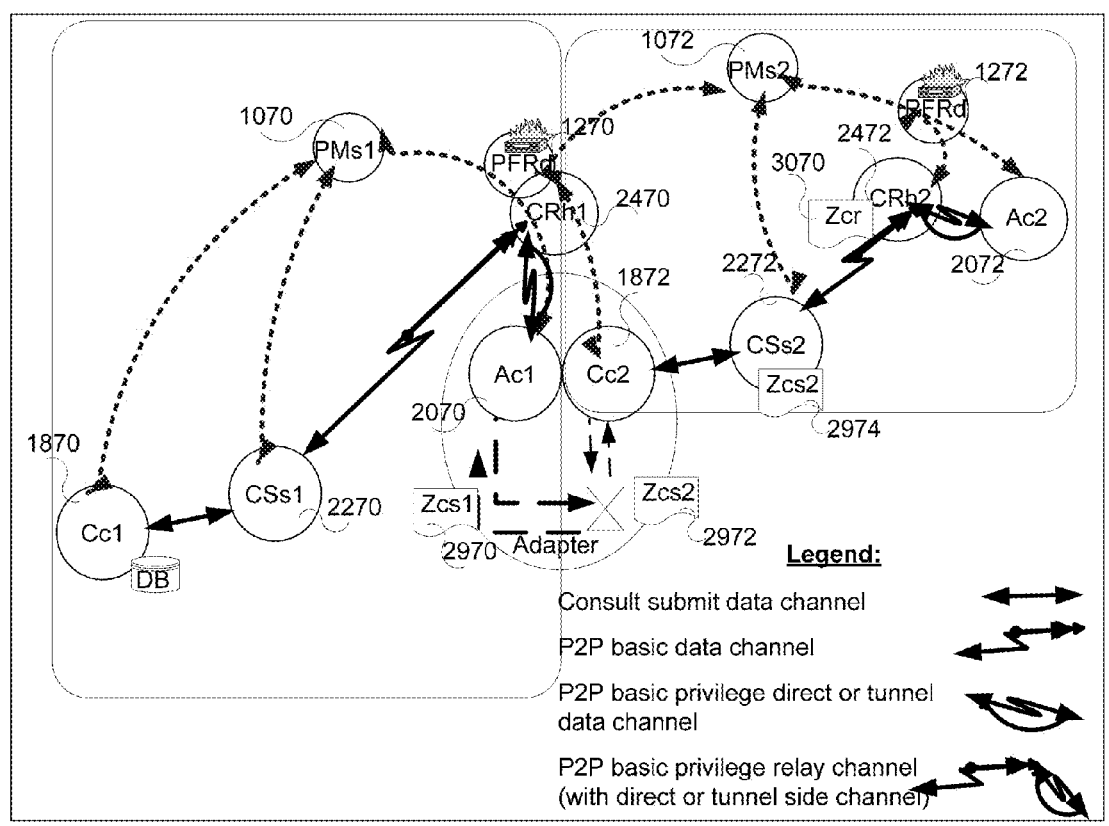
FIG. 7 illustrates an embodiment of systems and methods for a workflow to resolve a consult by submitting it into a posterior social network consultation domain.

An Embodiment for Case of Resubmission from a First Consultation Domain into a Second Consultation Domain FIG. 7 illustrates an embodiment of systems and methods for a workflow to resolve a consult by submitting it into a posterior social network consultation domain wherein an advisor in a 1st social network consultation domain gets a 1st submittal from a first consulter in the 1st social network consultation domain, extracts all or a portion of the submittal, resubmits the extraction into a 2nd social network consultation domain, gets resolution for the extraction in the 2nd social network consultation domain, and returns a final combined resolution for the 1st submittal. The resubmission is very common in case of higher level of expertise is required in a particular sub-specialty, or in case of resubmission to advisors speaking or working in a different language.

In FIG. 7, Ac1 2070 receives submittal Zcs1 2970 within a 1st social network consultation domain to the left of FIG. 7 from Cc1 1870, utilizes an adapter circuit provided by Cc2 1872 to extract all or a portion of Zcs1 2970 into Zcs2 2972 with format and syntax conformed to requirements of the 2nd social network consultation domain, submits the Zcs2 to Ac2 2072 for resolution, acquires the returned resolution in Zcr 3070, and proceeds to combine the resolution in Zcr 3070 into final resolution. It is apparent to those skilled in the art that once Zcr 3070 is acquired, all other activities in combining the resolution into a final resolution and returning the final resolution to 1st consulter in Cc1 1870 is apparent and is easily feasible. Hence, the identification of said activities is omitted in FIG. 7.

Figure 8:
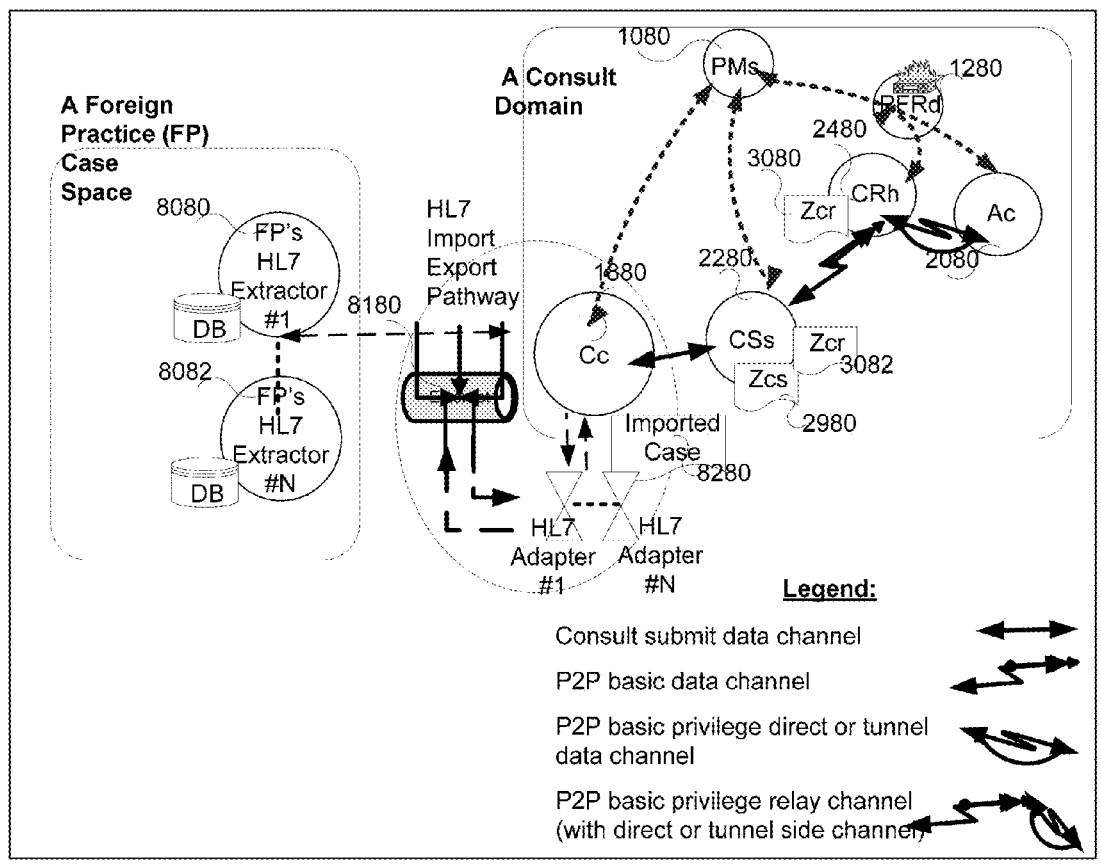
FIG. 8 illustrates an embodiment of systems and methods for a workflow to resolve a foreign case from an anterior foreign case space by submitting it into a consultation domain.

FIG. 8 illustrates an embodiment of systems and methods for a workflow to resolve a foreign case from an anterior foreign case space by converting said case into a consult, submitting it into a consultation domain and returning the resolution of said consult when it is closed.

In an aspect of FIG. 8, consulter Cc 1880 determines to submit a consult that is based on a case in a Foreign space, sends a request to Foreign Space HL7 extractor 8080 which has earlier registered to HL7 Import-Export pathway 8180, performs pulling through said pathway 8180 with support from said extractor 8080 to store Imported case 8280 in a local database, ready for submission to an advisor that is associated to CRh 2480. In another aspect of FIG. 8, said advisor who runs on Ac 2080 accomplishes Zcr 3080, returns a duplicate of said Zcr that is copied and stored as Zcr 3082 coupled with a resolution. Upon said consulter's request, Cc notifies said extractor 8080 to pull said resolution included in Zcr 3082 back to said Foreign space case. It is apparent to those skilled in the art that once an Imported case is acquired into local storage, all other activities in submitting a consult associated with the case and getting the resolution is apparent and is easily feasible. Hence, the identification of said activities is omitted in FIG. 8.

Exemplary Use Case Scenarios

FIG. 9 shows an exemplary flowchart to connect Np to PNp peers. First Np's X user logs into the PSs (5202). The PSs determines X's profile and sends to the Np (5204). The PNp's P user logs into the PSs (5206). The PNp applies s-token for P's VPN login to P's ordered PFRds, and if successful sets the port-forward to P's PNp host and the checks for PFRd success. If successful, the PNp updates P's profile with setting to allow VPN access privilege (5214) and otherwise the PNp updates P's profile with failed login profile (5212). From 5212 or 5214, NP's X and PNp's P users are known to be present and available for chatting in the social network.

Figure 10:
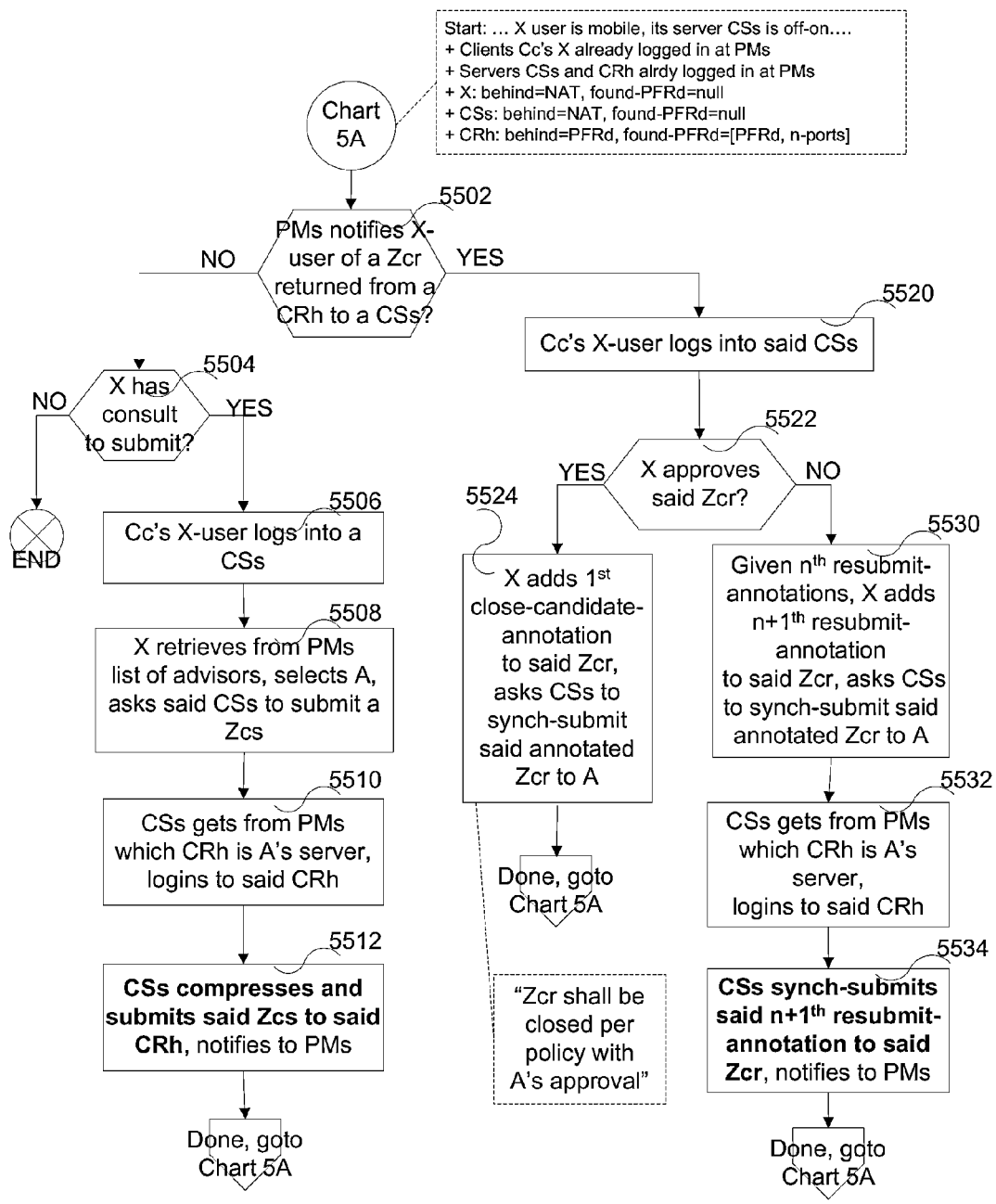
FIG. 10 shows an exemplary flowchart for a Cc user to submit a consult and sometime later fetch and approve its resolution.

FIG. 10 shows an exemplary flowchart, CHART 5A, for a Cc User to Submit and Approve Consultation Resolution. In this example, the user X is mobile, with clients Cc's X already logged in at PMs, and servers CSs and CRh already logged in at PMs. First, a condition is check if the PMs notifies X user of a Zcr returned from a CRh to a CSs (5502). If not, the system checks if X has a consultation case to submit (5504). Next, in 5506, Cc's X-user logs into a CSs, and X retrieves from the PMs a list of advisors, selects an advisor A, and ask the CSs to submit a Zcs (5508). The CSs gets from the PMs which CRh is A's server and logs into the CRh (5510). The CSs compresses and submits the Zcs to the CRh and notifies the PMs (5512) and proceeds to the operation in FIG. 5A. From 5502, if there is a Zcr returned, the Cc's X user logs into the CSs (5520) and checks if X approves the Zcr (5522). If approved, X adds the closed candidate annotation to the Zcr and asks the CSs to synch submit the annotation Zcr to A (5524) and the Zcr can then be closed per policy with A's approval (5526) and proceeds to FIG. 5A. If there is no approval, X adds the next resubmission annotation to the Zcr and asks the CSs to synch-submit the annotated Zcr to A (5530). The CSs gets from the PMs which CRh is A's server and logs in to the CRh (5532). The CSs synch submits the next resubmitted annotation to the Zcr and notifies the PMs (5534) and proceeds to CHART 5A.

Figure 11:
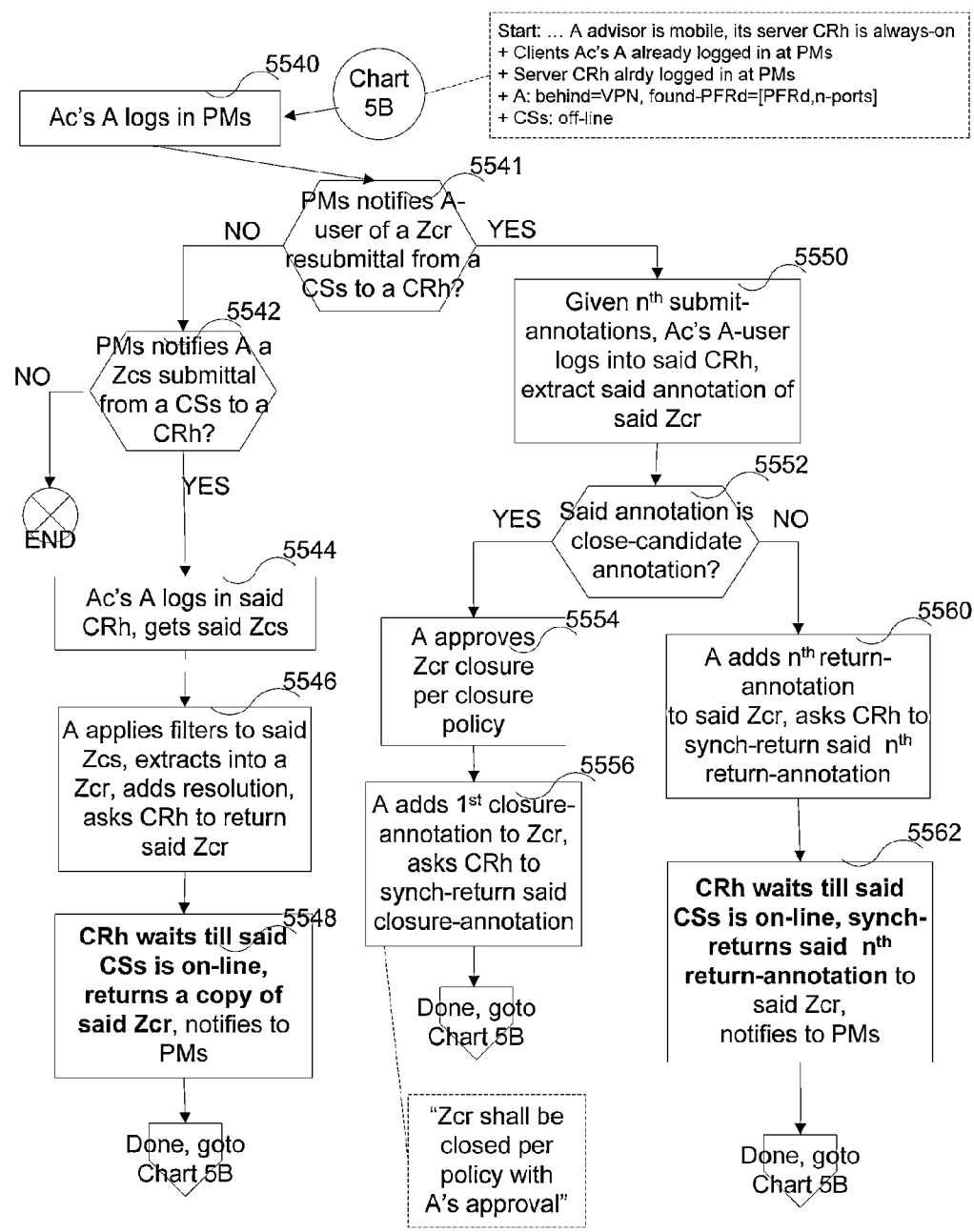
FIG. 11 shows an exemplary flowchart for an Ac user to fetch a consult submit, resolve and return it back, and sometime later fetch and approve said consult's closure.

FIG. 11 shows an exemplary flowchart, CHART 5B, for an Ac User to Resolve and Approve Consultation Closure. A user logs in to its server CRh (5540). The PMs process checks if for A user there is a Zcr resubmittal from a CSs to a CRh (5541). If not, the process checks if the PMs notifies A with a Zcs submittal from a CSs to a CRh and if not, the process exits, and alternatively, Ac's A logs in the CRh and gets the Zcs (5544). A applies filters to the Zcs and extracts files into a Zcr and adds resolution work and asks CRh to return the Zcr (5546). CRh waits till the CSs is on line and returns the Zcr and notifies the PMs (5548) and proceeds with CHART 5B. Alternatively, from 5540, upon a resubmitted annotation, Ac's A user logs in to the CRh and extracts annotations from the Zcr (5550). The user checks if the annotation is a close-candidate annotation (5552) and if so A approves the Zcr closure per closure policy (5554) and indicates that the Zcr shall be closed with A's approval (5556) and proceeds to FIG. 5B. From 5552, if the annotation is not closure, the process adds a return annotation to the Zcr and asks the CRh to synch return the return annotation (5560). The CRh waits for the CSs is on line and synch returns the return annotation to the Zcr and notifies the PMs (5562) and proceeds to CHART 5B.

The system uses a scalable, peer-peer social network system architecture with distributable servers, with upgradable framework to integrate new equipment and devices per clients' requests, and expandable strategy to add new clients. Moreover, the system also mediates the new clients' new practices and provides teleconsult service administrators the tools they need to gradually and effectively integrate new teleconsult service alongside with already available services. For example, the system can convert cases in one language to another language and updates the consultation domain.

Figure 12:
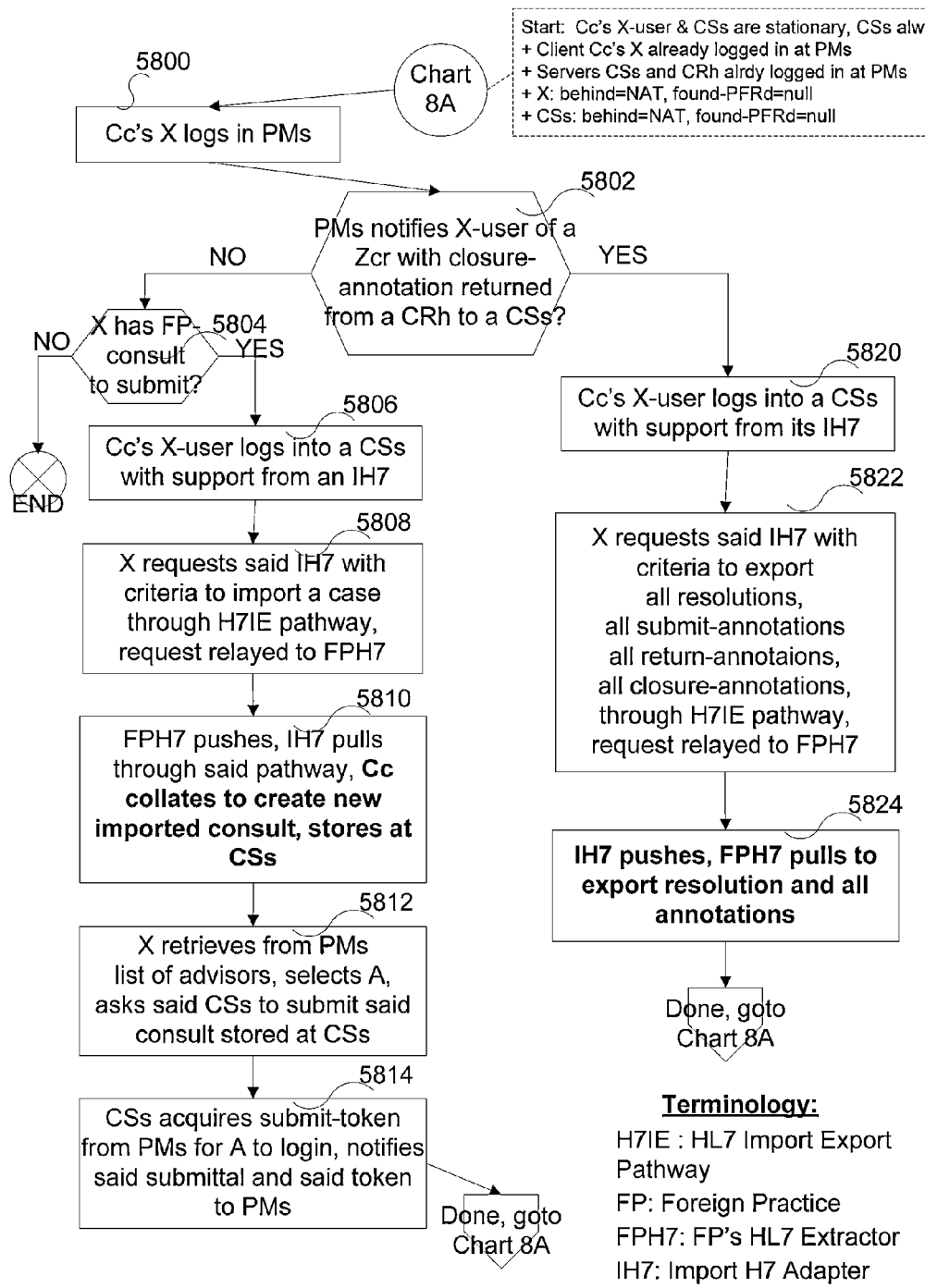
FIG. 12 shows an exemplary flowchart of an anterior mediation gateway wherein a case from a foreign case space is submitted into a consultation domain.

FIG. 12 shows an exemplary flowchart, CHART 8A, wherein a case from an anterior foreign case space is submitted into a consultation domain. In this process, after a user X logs in to a PMs from a Cc system, the process checks if the PMs has a Zcr with closure annotation sent from a CRh to a CSs which is to be notified to X (5802). If not, the process then checks if X has FP consults to submit (5804). If not, the process exits, and alternatively the Cc's X user logs in to a CSs with support from an IH7 (5806). X then requests the IH7 with criteria to import a case through an H7IE pathway, where said request is relayed to FPH7 (5808). FPH7 pushes, IH7 pulls, and Cc collates to create new imported consult (5810). X retrieves from PMs the list of advisors, selects A, and asks CSs to announce to A the submission of the consult stored at CSs (5812). Next, CSs acquires a submit-token from the PMs for later login by advisor A and notifies the submittal and the token to the PMs (5814). This step completes the submission of a case from a foreign case space into an advisor in said consultation domain. The process then returns to the beginning of CHART 8A.

Again from 5802, if a closure annotation has been returned, the Cc's X-user logs into a CSs with support from its IH7 (5820). X then requests IH7 with criteria to export all resolutions, submit annotations, return annotations, closure annotations through the H7IE pathway, and said request is also relayed to FPH7 (5822). Next, IH7 pushes and FPH7 pulls to export resolution and all annotations back to the original case in the foreign case space (5824). The case's resolution is done and is fully documented. The process then goes to CHART 8A to continue processing.

The system ensures confidentiality of protected health information (PHI) and renders the PHI unusable, unreadable, or indecipherable to unauthorized individuals. In one embodiment, the electronic PHI can be encrypted as specified in the HIPAA Security Rule by "the use of an algorithmic process to transform data into a form in which there is a low probability of assigning meaning without use of a confidential process or key" (45 CFR 164.304 definition of encryption) and such confidential process or key that might enable decryption has not been breached. To avoid a breach of the confidential process or key, these decryption tools are stored on a device or at a location separate from the data they are used to encrypt or decrypt. The encryption processes identified below can be used meet this standard.

(i) Valid encryption processes for data at rest consistent with NIST Special Publication 800-111, Guide to Storage Encryption Technologies for End User Devices.

(ii) Valid encryption processes for data in motion which comply, as appropriate, with NIST Special Publications 800-52, Guidelines for the Selection and Use of Transport Layer Security (TLS) Implementations; 800-77, Guide to IPsec VPNs; or 800-113, Guide to SSL VPNs, or others which are Federal Information Processing Standards (FIPS) 140-2 validated.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative of the invention and non-limiting and it will be understood by persons skilled in the art that other variants and modifications may be made without departing from the scope of the invention as defined in the claims appended hereto.

What is claimed is:

1. A system for multi-media multi-party conference communication, comprising: a processor; one or more multi-media encoding/decoding modules to support processing/transcoding multi-media text/file/audio/video for conferencing communication; code for retrieving a plurality of communication attributes for a peer client used by a user to log in and stay present, wherein said client program is an end-user program or a server program, and wherein said program is configured with privilege access to a list of public known routers; and code for processing said communication attributes coupled with validation through executing dynamic IP address learning techniques to determine an addressing mode for said user, wherein said addressing mode is a private addressing mode (associated with NATed type), or a public addressing mode (associated with Privileged NATed type), coupled with an assigned ordered set of privilege public routers for establishing communication in the case of public addressing mode; the system further comprising: code for video conference communication to other systems in other social network addressing domains coupled with other social network processing systems; code for establishing and running communication channels for text/file/audio/video/game/data chatting for 2-party P2P basic bridging between two user peer clients or between a user peer client and a server peer client, further including code for a Privileged NATed type peer to execute a plurality of instructions to authenticate itself to a public router associated with a privilege using a secured transport protocol associated with said privilege, set port-forwarding for a range of public ports on said public router to itself using a plurality of instructions of a port control protocol; code for switching communication channels from communication channels provided by a basic router supporting 2-way P2P basic privilege relay channel to communication channels provided by a tagged architecture router supporting PnP tagged privilege relay channel in an assigned public router list if a third peer user client is added to the conference bridge of at least two peer user clients; and multimedia input/output devices including at least a camera and a microphone to support text/file/audio/video conferencing communication; and code for embedding tag information into data packets before sending a stream of multimedia data packets to a conference bridge on a router and demultiplexing participant streams from a conference bridge on said router based on embedded tag information according to the requirement of a tagged architecture conference bridge at an assigned public router for directing a request for adding or removing a new participant to the conference bridge to an assigned Privileged NATed peer, wherein at least one of a plurality of the peer clients is a Privileged NATed peer associated with public addressing mode.

2. The system of claim 1, further comprising a conferee server or requestor server including: a database server; code for determining addressing mode, private addressing mode or public addressing mode; code for accepting login from a conferee or from a moderator or from an advisor server acting on behalf of the moderator or an advisor; code for logging in to a moderator or an advisor server on behalf of a requestor; code for storing and forwarding a compressed media representing a submittal or an annotation of various type; code for receiving a compressed media representing a resolution or an annotation; an uptime attribute, wherein said system is always-on or off-on dynamically; code for logging in to said moderator or advisor servers of interest using a 2-way P2P basic privilege relay channel with direct side channel to the advisor server; and code for submitting consultations and receiving resolutions.

3. The system of claim 1, further comprising a moderator or advisor server including: a database server; code for asserting addressing mode is public addressing mode; code for logging in to an requestor server on behalf of a moderator or advisor; code for accepting login from an advisor or from a requestor server acting on behalf of a conferee or requestor; code for receiving a compressed media representing a submittal or an annotation of various type; code for storing and forwarding a compressed media representing a resolution, or an annotation of various type; code for monitoring the up or down status of a plurality of requestor servers of interest due to instructions from an advisor; code for logging in to said requestor servers of interest using a 2-way P2P basic privilege direct channel to the advisor server; and code for receiving consultations and returning resolutions.

4. The system of claim 2, wherein the conferee server includes code for adapting a case in a foreign space into local data store ready for consult submitting in the social network consult domain, wherein the adapter module is based on multi-domainstandard conversion technology including in multi-domain record conversion for medical data HL7—Health Level 7; and code for exporting a resolution from the social network consult domain into a case in a foreign space wherein the exporter module is based on multi-domainstandard conversion technology including inmulti-domain record conversion for medical data HL7—Health Level 7.

5. The system of claim 1, further comprising a privilege moderator including: code to log into an associated advisor server via a P2P basic privilege direct data channel if said advisor server is not directly attached to the local area network (LAN) segment of the router, and otherwise to log into said advisor server using a P2P basic privilege tunnel data channel; and code to log into a conferee server and keep a P2P basic privilege relay channel relayed by a public router connected with a conferee server with a tunnel side channel to the advisor if the advisor system is not directly attached to the local area network (LAN) segment of the router; otherwise code to log into the conferee server relayed through a public router connected with the conferee server and keep a P2P basic privilege relay channel with a direct side channel to the advisor.

6. A multi-media multi-party communication conference bridging equipment, comprising: a router with a public address if operating in WAN/Internet, or a well-known address if operating in a LAN or VPN environment; one or more multi-media encoding/decoding modules to support processing/transcoding multi-media text/file/audio/video for conferencing communication; code for storing and interpreting a privilege assigned to a user; and code for duplicating tagged data packets of a participant's incoming stream and multiplexing said duplicated data packets into other participants' outgoing streams according to requirements of a tagged architecture if it is supported by said router; wherein said router is communicatively coupled with, and routes network communication for, the system of claim 1.

7. The equipment of claim 6, further comprising code to receive and authenticate a login user via a required security transport protocol associated with a privilege for said user, and to execute instructions of a port control protocol from said user to configure port-forwarding of a plurality of public address ports to said user for case of P2P basic 2-party bridge.

8. The equipment of claim 7, further comprising code to receive and authenticate a login user via a required security transport protocol associated with a privilege for said user, execute instructions from said user to add or remove participants in a tagged architecture conference bridge, configure routing paths of a plurality of public address ports of said conference bridge to participants for case of tagged PnP multi-party conference bridge.

9. A multi-media multi-party conference network system coupled to a social network and a social network processing system, comprising: one or more multi-media encoding/decoding modules to support processing/transcoding multi-media text/file/audio/video for conferencing communication; at least one of a plurality of video conferencing equipment; at least two (2) of a plurality of systems as cited in claim 1; and code for the management of said plurality of video conference equipment, said management includes a health status, percent loading factor status, net effective relative distance in number of hops calculated from a dynamic topology scan to collect the location of network entities, and configuration privilege for N-way video conference to determine a preferred ordered list of a plurality of said video conference equipment for a peer network entity to use to establish connectivity channel.

* * * * *